US012667388B2

(12) United States Patent
Lindekugel et al.

(10) Patent No.: US 12,667,388 B2
(45) Date of Patent: Jun. 30, 2026

(54) STEP NEEDLE FOR INTRAOSSEOUS ACCESS DEVICE

(71) Applicant: Bard Access Systems, Inc., Salt Lake City, UT (US)

(72) Inventors: Eric W. Lindekugel, Salt Lake City, UT (US); Daniel B. Blanchard, Bountiful, UT (US); Jay A. Muse, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 29 days.

(21) Appl. No.: 18/826,015

(22) Filed: Sep. 5, 2024

(65) Prior Publication Data

US 2024/0423668 A1     Dec. 26, 2024

Related U.S. Application Data

(62) Division of application No. 17/033,093, filed on Sep. 25, 2020, now Pat. No. 12,082,843.

(Continued)

(51) Int. Cl.
*A61B 17/34*         (2006.01)
*A61B 90/00*         (2016.01)

(52) U.S. Cl.
CPC ...... *A61B 17/3478* (2013.01); *A61B 17/3472* (2013.01); *A61B 17/3496* (2013.01); *A61B 2090/034* (2016.02)

(58) Field of Classification Search
CPC ............ A61B 17/1615; A61B 17/1626; A61B 17/1628; A61B 17/164; A61B 17/34;

(Continued)

(56) References Cited

U.S. PATENT DOCUMENTS 2,409,979 A    10/1946  Huber
2,773,501 A    12/1956  Young
              (Continued)

FOREIGN PATENT DOCUMENTS

EP        0232600 A1    8/1987
EP        0548612 A1    6/1993
              (Continued)

OTHER PUBLICATIONS

PCT/US2025/030820 filed May 23, 2025 International Search Report and Written Opinion dated Jul. 23, 2025.

(Continued)

*Primary Examiner* — Ryan J. Severson
(74) *Attorney, Agent, or Firm* — Rutan & Tucker LLP

(57)          ABSTRACT

An apparatus and method for a stepped needle for an intraosseous device that uses the outer surface of the bone cortex as a reference point. Since the thickness of the bone cortex does not vary significantly between patients, the accuracy of needle placement can be improved. The device includes a needle with a stepped increase in outer diameter disposed along the needle shaft. The abrupt change in outer diameter provides a substantial increase in insertion force. The stepped increase prevents any further insertion into the bone cortex. Embodiments can include a tapered needle lumen for medullary access confirmation and an overtube that is rotatably and slidably engaged to protect surrounding tissues and prevent needle stick injuries. Further, a needle hub can be rotatable or slidable, and can transition an overtube to an extended position to prevent accidental needle stick injuries.

25 Claims, 10 Drawing Sheets

Related U.S. Application Data

(60) Provisional application No. 62/907,450, filed on Sep. 27, 2019.

(58) Field of Classification Search
CPC ............ A61B 17/3401; A61B 17/3417; A61B 17/3472; A61B 17/3478; A61B 17/348; A61B 17/3496; A61B 2017/3433; A61B 2017/3492; A61B 2090/033; A61B 2090/034
See application file for complete search history.

(56) References Cited

U.S. PATENT DOCUMENTS

| | | | |
|---|---|---|---|
| 3,071,135 A | 1/1963 | Baldwin et al. |
| 3,166,189 A | 1/1965 | Disston |
| 3,329,261 A | 7/1967 | Serany, Jr. et al. |
| D222,312 S | 10/1971 | Kurtz et al. |
| 3,802,555 A | 4/1974 | Grasty et al. |
| 3,815,605 A | 6/1974 | Schmidt et al. |
| 3,991,765 A | 11/1976 | Cohen |
| 4,010,737 A | 3/1977 | Vilaghy et al. |
| 4,153,160 A | 5/1979 | Leigh |
| 4,226,328 A | 10/1980 | Beddow |
| 4,266,555 A | 5/1981 | Jamshidi |
| 4,314,565 A | 2/1982 | Lee |
| 4,383,530 A | 5/1983 | Bruno |
| 4,501,363 A | 2/1985 | Isbey, Jr. |
| 4,513,754 A | 4/1985 | Lee |
| 4,595,102 A | 6/1986 | Cianci et al. |
| 4,838,282 A | 6/1989 | Strasser et al. |
| 4,889,529 A | 12/1989 | Haindl |
| 4,925,448 A | 5/1990 | Bazaral |
| 4,952,207 A | 8/1990 | Lemieux |
| 4,964,854 A | 10/1990 | Luther |
| 4,969,870 A | 11/1990 | Kramer et al. |
| 5,040,542 A | 8/1991 | Gray |
| 5,042,558 A | 8/1991 | Hussey et al. |
| 5,053,017 A | 10/1991 | Chamuel |
| 5,098,391 A | 3/1992 | Pantages et al. |
| 5,122,114 A | 6/1992 | Miller et al. |
| 5,207,697 A | 5/1993 | Carusillo et al. |
| 5,263,939 A | 11/1993 | Wortrich |
| 5,290,267 A | 3/1994 | Zimmermann |
| 5,312,364 A | 5/1994 | Jacobs |
| 5,322,163 A | 6/1994 | Foos |
| 5,332,398 A | 7/1994 | Miller et al. |
| 5,364,367 A | 11/1994 | Banks et al. |
| 5,372,583 A | 12/1994 | Roberts et al. |
| 5,406,940 A | 4/1995 | Melzer et al. |
| 5,451,210 A | 9/1995 | Kramer et al. |
| 5,507,751 A | 4/1996 | Goode et al. |
| 5,525,314 A | 6/1996 | Hurson |
| 5,554,154 A | 9/1996 | Rosenberg |
| 5,575,780 A | 11/1996 | Saito |
| 5,591,188 A | 1/1997 | Waisman |
| 5,601,559 A | 2/1997 | Melker et al. |
| 5,688,249 A | 11/1997 | Chang et al. |
| 5,746,720 A | 5/1998 | Stouder, Jr. |
| 5,772,678 A | 6/1998 | Thomason et al. |
| 5,779,708 A | 7/1998 | Wu |
| 5,807,275 A | 9/1998 | Jamshidi |
| 5,810,738 A | 9/1998 | Thomas, II |
| 5,810,826 A | 9/1998 | Åkerfeldt et al. |
| 5,817,052 A | 10/1998 | Johnson et al. |
| 5,853,393 A | 12/1998 | Bogert |
| 5,868,684 A | 2/1999 | Åkerfeldt et al. |
| 5,868,711 A | 2/1999 | Kramer et al. |
| 5,871,470 A | 2/1999 | McWha |
| 5,885,293 A | 3/1999 | McDevitt |
| 5,927,976 A | 7/1999 | Wu |
| 5,947,890 A | 9/1999 | Spencer et al. |
| 5,960,797 A | 10/1999 | Kramer et al. |
| 5,967,143 A | 10/1999 | Klappenberger |
| 5,990,382 A | 11/1999 | Fox |
| 6,012,586 A | 1/2000 | Misra |
| 6,068,121 A | 5/2000 | McGlinch |
| 6,117,108 A | 9/2000 | Woehr et al. |
| 6,135,769 A | 10/2000 | Kwan |
| 6,210,373 B1 | 4/2001 | Allmon |
| 6,210,376 B1 | 4/2001 | Grayson |
| 6,228,088 B1 | 5/2001 | Miller et al. |
| 6,247,928 B1 | 6/2001 | Meller et al. |
| 6,273,715 B1 | 8/2001 | Meller et al. |
| 6,419,490 B1 | 7/2002 | Kitchings, Jr. |
| 6,458,117 B1 | 10/2002 | Pollins, Sr. |
| 6,527,778 B2 | 3/2003 | Athanasiou et al. |
| 6,602,214 B2 | 8/2003 | Heinz et al. |
| 6,626,887 B1 | 9/2003 | Wu |
| 6,629,959 B2 | 10/2003 | Kuracina et al. |
| 6,641,395 B2 | 11/2003 | Kumar et al. |
| 6,652,490 B2 | 11/2003 | Howell |
| 6,692,471 B2 | 2/2004 | Boudreaux |
| 6,761,726 B1 | 7/2004 | Findlay et al. |
| 6,814,734 B2 | 11/2004 | Chappuis et al. |
| 6,830,562 B2 | 12/2004 | Mogensen et al. |
| 6,875,219 B2 | 4/2005 | Arramon et al. |
| 6,905,486 B2 | 6/2005 | Gibbs |
| 6,916,292 B2 | 7/2005 | Morawski et al. |
| 6,984,213 B2 | 1/2006 | Horner et al. |
| 6,991,096 B2 | 1/2006 | Gottlieb et al. |
| 6,997,907 B2 | 2/2006 | Safabash et al. |
| 7,112,191 B2 | 9/2006 | Daga |
| 7,135,031 B2 | 11/2006 | Flint |
| 7,179,244 B2 | 2/2007 | Smith et al. |
| 7,214,208 B2 | 5/2007 | Vaillancourt et al. |
| 7,278,987 B2 | 10/2007 | Solazzo |
| 7,347,838 B2 | 3/2008 | Kulli |
| 7,347,840 B2 | 3/2008 | Findlay et al. |
| 7,399,306 B2 | 7/2008 | Reiley et al. |
| 7,407,493 B2 | 8/2008 | Cane' |
| 7,410,053 B2 | 8/2008 | Bowen et al. |
| 7,434,687 B2 | 10/2008 | Itou et al. |
| 7,458,954 B2 | 12/2008 | Ferguson et al. |
| 7,513,888 B2 | 4/2009 | Sircom et al. |
| 7,530,965 B2 | 5/2009 | Villa et al. |
| 7,534,227 B2 | 5/2009 | Kull |
| 7,569,033 B2 | 8/2009 | Greene et al. |
| 7,582,102 B2 | 9/2009 | Heinz et al. |
| 7,588,559 B2 | 9/2009 | Aravena et al. |
| 7,658,725 B2 | 2/2010 | Bialecki et al. |
| 7,670,328 B2 | 3/2010 | Miller |
| 7,699,807 B2 | 4/2010 | Faust et al. |
| 7,699,850 B2 | 4/2010 | Miller |
| 7,736,332 B2 | 6/2010 | Carlyon et al. |
| 7,743,918 B2 | 6/2010 | Itou et al. |
| 7,749,225 B2 | 7/2010 | Chappuis et al. |
| 7,798,994 B2 | 9/2010 | Brimhall |
| 7,811,260 B2 | 10/2010 | Miller et al. |
| 7,815,642 B2 | 10/2010 | Miller |
| 7,828,773 B2 | 11/2010 | Swisher et al. |
| 7,828,774 B2 | 11/2010 | Harding et al. |
| 7,833,204 B2 | 11/2010 | Picha |
| 7,842,038 B2 | 11/2010 | Haddock et al. |
| 7,850,620 B2 | 12/2010 | Miller et al. |
| 7,850,650 B2 | 12/2010 | Breitweiser |
| D633,199 S | 2/2011 | MacKay et al. |
| 7,899,528 B2 | 3/2011 | Miller et al. |
| 7,900,549 B2 | 3/2011 | Kobayashi |
| 7,905,857 B2 | 3/2011 | Swisher |
| 7,951,089 B2 | 5/2011 | Miller |
| 7,955,297 B2 | 6/2011 | Radmer et al. |
| 7,972,339 B2 | 7/2011 | Nassiri et al. |
| 7,976,498 B2 | 7/2011 | Swisher et al. |
| 7,976,502 B2 | 7/2011 | Baid |
| 8,038,664 B2 | 10/2011 | Miller et al. |
| 8,043,253 B2 | 10/2011 | Kraft et al. |
| 8,043,265 B2 | 10/2011 | Abe et al. |
| 8,096,973 B2 | 1/2012 | Snow et al. |
| 8,142,365 B2 | 3/2012 | Miller |
| 8,152,771 B2 | 4/2012 | Mogensen et al. |
| 8,162,904 B2 | 4/2012 | Takano et al. |
| 8,167,899 B2 | 5/2012 | Justis et al. |
| 8,231,547 B2 | 7/2012 | Deck et al. |

(56)                    References Cited

U.S. PATENT DOCUMENTS

| | | | |
|---|---|---|---|
| 8,235,945 B2 | 8/2012 | Baid |
| 8,240,468 B2 | 8/2012 | Wilkinson et al. |
| 8,246,584 B2 | 8/2012 | Aravena et al. |
| 8,273,053 B2 | 9/2012 | Saltzstein |
| 8,292,891 B2 | 10/2012 | Browne et al. |
| 8,308,693 B2 | 11/2012 | Miller et al. |
| 8,333,769 B2 | 12/2012 | Browne et al. |
| 8,356,598 B2 | 1/2013 | Rumsey |
| 8,357,163 B2 | 1/2013 | Sidebotham et al. |
| 8,388,623 B2 | 3/2013 | Browne et al. |
| 8,414,539 B1 | 4/2013 | Kuracina et al. |
| 8,419,683 B2 | 4/2013 | Miller et al. |
| 8,480,632 B2 | 7/2013 | Miller et al. |
| 8,480,672 B2 | 7/2013 | Browne et al. |
| 8,486,027 B2 | 7/2013 | Findlay et al. |
| 8,506,568 B2 | 8/2013 | Miller |
| 8,529,576 B2 | 9/2013 | Krueger et al. |
| 8,535,271 B2 | 9/2013 | Fuchs et al. |
| 8,562,615 B2 | 10/2013 | Browne et al. |
| 8,584,849 B2 | 11/2013 | McCaffrey |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tal et al. |
| 8,662,306 B2 | 3/2014 | Agrawal |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,758,383 B2 | 6/2014 | Geist |
| 8,771,230 B2 | 7/2014 | White et al. |
| 8,801,663 B2 | 8/2014 | Woehr |
| 8,812,101 B2 | 8/2014 | Miller et al. |
| 8,814,835 B2 | 8/2014 | Baid |
| 8,828,001 B2 | 9/2014 | Stearns et al. |
| 8,870,872 B2 | 10/2014 | Miller |
| 8,893,883 B2 | 11/2014 | Valaie et al. |
| D720,471 S | 12/2014 | Angel et al. |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,131,925 B2 | 9/2015 | Kraft et al. |
| 9,149,625 B2 | 10/2015 | Woehr et al. |
| 9,173,679 B2 | 11/2015 | Tzachar et al. |
| 9,186,217 B2 | 11/2015 | Goyal |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,451,968 B2 | 9/2016 | Miller et al. |
| 9,451,983 B2 | 9/2016 | Windolf |
| 9,480,483 B2 | 11/2016 | Browne et al. |
| 9,486,604 B2 | 11/2016 | Murray et al. |
| 9,504,477 B2 | 11/2016 | Miller et al. |
| 9,545,243 B2 | 1/2017 | Miller et al. |
| 9,615,816 B2 | 4/2017 | Woodard |
| 9,615,838 B2 | 4/2017 | Nino et al. |
| 9,623,210 B2 | 4/2017 | Woehr |
| 9,636,484 B2 | 5/2017 | Baid |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,744,333 B2 | 8/2017 | Terzibashian |
| 9,782,546 B2 | 10/2017 | Woehr |
| 9,788,843 B2 | 10/2017 | Teisen et al. |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 9,999,444 B2 | 6/2018 | Geist et al. |
| 10,022,464 B2 | 7/2018 | Sarphati et al. |
| 10,039,897 B2 | 8/2018 | Norris et al. |
| 10,052,111 B2 | 8/2018 | Miller et al. |
| 10,064,694 B2 | 9/2018 | Connolly |
| 10,070,933 B2 | 9/2018 | Adler et al. |
| 10,070,934 B2 | 9/2018 | Kerns et al. |
| 10,080,864 B2 | 9/2018 | Terzibashian |
| 10,092,320 B2 | 10/2018 | Morgan et al. |
| 10,106,295 B2 | 10/2018 | Lockwood |
| 10,130,343 B2 | 11/2018 | Miller et al. |
| 10,136,878 B2 | 11/2018 | Tzachar et al. |
| 10,182,878 B2 | 1/2019 | Goyal |
| 10,238,420 B2 | 3/2019 | Karve et al. |
| 10,245,010 B2 | 4/2019 | Miller et al. |
| 10,251,812 B2 | 4/2019 | Tomes et al. |
| 10,258,783 B2 | 4/2019 | Miller et al. |
| 10,314,629 B2 | 6/2019 | Park et al. |
| 10,405,938 B2 | 9/2019 | Ramsey |
| 10,441,454 B2 | 10/2019 | Tanghoej et al. |
| 10,456,149 B2 | 10/2019 | Miller |
| 10,456,497 B2 | 10/2019 | Howell et al. |
| 10,595,896 B2 | 3/2020 | Miller |
| 10,722,247 B2 | 7/2020 | Browne et al. |
| 10,893,887 B2 | 1/2021 | Blanchard |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0162559 A1 | 8/2004 | Arramon et al. |
| 2004/0220497 A1 | 11/2004 | Findlay et al. |
| 2004/0243135 A1 | 12/2004 | Koseki |
| 2004/0260246 A1 | 12/2004 | Desmond |
| 2005/0033235 A1 | 2/2005 | Flint |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0148940 A1 | 7/2005 | Miller |
| 2005/0165403 A1 | 7/2005 | Miller |
| 2005/0261693 A1 | 11/2005 | Miller et al. |
| 2006/0015066 A1 | 1/2006 | Turieo et al. |
| 2006/0025723 A1 | 2/2006 | Ballarini |
| 2007/0010843 A1 | 1/2007 | Green |
| 2007/0016138 A1 | 1/2007 | Swisher et al. |
| 2007/0049945 A1 | 3/2007 | Miller |
| 2007/0191772 A1 | 8/2007 | Wojcik |
| 2007/0270775 A1 | 11/2007 | Miller et al. |
| 2008/0086142 A1 | 4/2008 | Kohm et al. |
| 2008/0119759 A1 | 5/2008 | McLain |
| 2008/0119821 A1 | 5/2008 | Agnihotri et al. |
| 2008/0140014 A1 | 6/2008 | Miller et al. |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0105775 A1 | 4/2009 | Mitchell et al. |
| 2009/0118639 A1 | 5/2009 | Moos et al. |
| 2009/0204024 A1 | 8/2009 | Miller |
| 2009/0228014 A1 | 9/2009 | Stearns et al. |
| 2009/0306697 A1 | 12/2009 | Fischvogt |
| 2010/0030105 A1 | 2/2010 | Noishiki et al. |
| 2010/0082033 A1 | 4/2010 | Germain |

(56)                     References Cited

U.S. PATENT DOCUMENTS

| 2010/0152616 A1 | 6/2010 | Beyhan et al. |
| 2010/0185161 A1 | 7/2010 | Pellegrino et al. |
| 2010/0204649 A1 | 8/2010 | Miller et al. |
| 2010/0268241 A1 | 10/2010 | Flom et al. |
| 2010/0280410 A1 | 11/2010 | Moos et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0137253 A1 | 6/2011 | Simonton et al. |
| 2012/0041454 A1 | 2/2012 | Johnstone |
| 2012/0202180 A1 | 8/2012 | Stock et al. |
| 2012/0203154 A1 | 8/2012 | Tzachar |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0079720 A1 | 3/2013 | Finnestad et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2013/0331840 A1 | 12/2013 | Teisen et al. |
| 2014/0039400 A1 | 2/2014 | Browne et al. |
| 2014/0046327 A1 | 2/2014 | Tzachar et al. |
| 2014/0074102 A1 | 3/2014 | Mandeen et al. |
| 2014/0081281 A1 | 3/2014 | Felder |
| 2014/0142577 A1 | 5/2014 | Miller |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276366 A1 | 9/2014 | Bourne et al. |
| 2014/0276471 A1 | 9/2014 | Emery et al. |
| 2014/0276833 A1 | 9/2014 | Larsen et al. |
| 2014/0276839 A9 | 9/2014 | Forman et al. |
| 2014/0276927 A1 | 9/2014 | Barker |
| 2014/0343454 A1 | 11/2014 | Miller et al. |
| 2014/0343497 A1 | 11/2014 | Baid |
| 2015/0011941 A1 | 1/2015 | Saeki |
| 2015/0126931 A1 | 5/2015 | Holm et al. |
| 2015/0127006 A1 | 5/2015 | Miller |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0058432 A1 | 3/2016 | Miller |
| 2016/0066954 A1 | 3/2016 | Miller et al. |
| 2016/0106441 A1 | 4/2016 | Teisen et al. |
| 2016/0136410 A1 | 5/2016 | Aklog et al. |
| 2016/0183974 A1 | 6/2016 | Miller |
| 2016/0228676 A1 | 8/2016 | Glithero et al. |
| 2016/0235949 A1 | 8/2016 | Baid |
| 2016/0354539 A1 | 12/2016 | Tan et al. |
| 2016/0361519 A1 | 12/2016 | Teoh et al. |
| 2017/0021138 A1 | 1/2017 | Sokolski |
| 2017/0043135 A1 | 2/2017 | Knutsson |
| 2017/0056122 A1 | 3/2017 | Ramsey |
| 2017/0105763 A1 | 4/2017 | Karve et al. |
| 2017/0136217 A1 | 5/2017 | Riesenberger et al. |
| 2017/0143395 A1 | 5/2017 | Park et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0303962 A1 | 10/2017 | Browne et al. |
| 2017/0303963 A1 | 10/2017 | Kilcoin et al. |
| 2018/0092662 A1 | 4/2018 | Rioux et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0154112 A1 | 6/2018 | Chan et al. |
| 2018/0206933 A1 | 7/2018 | Healey et al. |
| 2018/0221564 A1 | 8/2018 | Patel et al. |
| 2018/0236182 A1 | 8/2018 | Charlebois et al. |
| 2018/0256209 A1 | 9/2018 | Muse et al. |
| 2019/0021807 A1 | 1/2019 | Barnell et al. |
| 2019/0060607 A1 | 2/2019 | Yabu et al. |
| 2019/0076132 A1 | 3/2019 | Tzachar et al. |
| 2019/0125404 A1 | 5/2019 | Shippert |
| 2019/0150953 A1 | 5/2019 | Budyansky et al. |
| 2019/0151606 A1 | 5/2019 | Mottola et al. |
| 2019/0201053 A1 | 7/2019 | Ben Mocha et al. |
| 2019/0223930 A1 | 7/2019 | Nolan et al. |
| 2019/0282244 A1 | 9/2019 | Muse |
| 2019/0328370 A1 | 10/2019 | Muse |
| 2019/0343556 A1 | 11/2019 | Coppedge et al. |
| 2021/0093358 A1 | 4/2021 | Lindekugel et al. |
| 2021/0137558 A1 | 5/2021 | Lindekugel |
| 2024/0050126 A1 | 2/2024 | Blanchard |
| 2025/0099133 A1 | 3/2025 | Lindekugel |
| 2025/0177001 A1 | 6/2025 | Blanchard |
| 2025/0359893 A1 | 11/2025 | Prakash et al. |

FOREIGN PATENT DOCUMENTS

| WO | 1997024151 A1 | 7/1997 |
| WO | 1998052638 A3 | 2/1999 |
| WO | 2004000408 A1 | 12/2003 |
| WO | 2004073500 A2 | 9/2004 |
| WO | 05041790 A2 | 5/2005 |
| WO | 2005046769 A2 | 5/2005 |
| WO | 2005053506 A2 | 6/2005 |
| WO | 2005072625 A2 | 8/2005 |
| WO | 2006047737 A2 | 5/2006 |
| WO | 2007018809 A2 | 2/2007 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011097311 A2 | 8/2011 |
| WO | 2011139294 A1 | 11/2011 |
| WO | 2013009901 A2 | 1/2013 |
| WO | 2013173360 A1 | 11/2013 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015177612 A1 | 11/2015 |
| WO | 2016033016 A1 | 3/2016 |
| WO | 16053834 A1 | 4/2016 |
| WO | 2016163939 A1 | 10/2016 |
| WO | 2018006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019051412 A1 | 3/2019 |
| WO | 2019164990 A1 | 8/2019 |
| WO | 2019215705 A1 | 11/2019 |
| WO | 2020012051 A1 | 1/2020 |
| WO | 2021062215 A1 | 4/2021 |

(56)     References Cited

FOREIGN PATENT DOCUMENTS

| WO | 2021173649 | A1 | 9/2021 |
| WO | 2022231609 | A1 | 11/2022 |
| WO | 2025245473 | A1 | 11/2025 |

OTHER PUBLICATIONS

U.S. Appl. No. 18/383,802, filed Oct. 25, 2023 Notice of Allowance dated Sep. 2, 2025.

U.S. Appl. No. 17/378,304, filed Jul. 16, 2021 Notice of Allowance dated Oct. 9, 2024.

U.S. Appl. No. 18/383,802, filed Oct. 25, 2023 Non-Final Office Action dated Apr. 1, 2025.

U.S. Appl. No. 18/383,802, filed Oct. 25, 2023 Restriction Requirement dated Nov. 5, 2024.

EP 17861304.8 filed Apr. 16, 2019 Extended European Search Report filed Jul. 28, 2020.

EP 17864208.8 filed May 24, 2019 Extended European Search Report filed May 19, 2020.

EP 20868558.6 filed Apr. 21, 2022 Extended European Search Report dated Aug. 11, 2023.

PCT/US 17/57270 filed Oct. 18, 2017 International Search Report and Written Opinion dated Jan. 12, 2018.

PCT/US2017/058863 filed Oct. 27, 2017 International Search Report and Written Opinion dated Jan. 29, 2018.

PCT/US2018/021398 filed Mar. 7, 2018 International search report and written opinion dated May 21, 2018.

PCT/US2020/052809 filed Sep. 25, 2020 International Search Report and Written Opinion dated Jan. 5, 2021.

PCT/US2021/019388 filed Feb. 24, 2021 International Search Report and Written Opinion dated May 17, 2021.

PCT/US2021/042040 filed Jul. 16, 2021 International Search Report and Written Opinion dated Oct. 4, 2021.

U.S. Appl. No. 15/796,471, filed Oct. 27, 2017 Advisory Action dated Jun. 15, 2020.

U.S. Appl. No. 15/796,471, filed Oct. 27, 2017 Final Office Action dated Apr. 23, 2020.

U.S. Appl. No. 15/796,471, filed Oct. 27, 2017 Non-Final Office Action dated Oct. 30, 2019.

U.S. Appl. No. 15/796,471, filed Oct. 27, 2017 Notice of Allowance dated Jun. 15, 2020.

U.S. Appl. No. 15/796,471, filed Oct. 27, 2017 Restriction Requirement dated Jul. 8, 2019.

U.S. Appl. No. 17/033,093, filed Sep. 25, 2020 Advisory Action dated Oct. 4, 2023.

U.S. Appl. No. 17/033,093, filed Sep. 25, 2020 Final Office Action dated Feb. 15, 2024.

U.S. Appl. No. 17/033,093, filed Sep. 25, 2020 Final Office Action dated Sep. 8, 2023.

U.S. Appl. No. 17/033,093, filed Sep. 25, 2020 Non-Final Office Action dated Mar. 2, 2023.

U.S. Appl. No. 17/033,093, filed Sep. 25, 2020 Non-Final Office Action dated Nov. 8, 2023.

U.S. Appl. No. 17/033,093, filed Sep. 25, 2020 Notice of Allowance dated Apr. 30, 2024.

U.S. Appl. No. 17/033,093, filed Sep. 25, 2020 Restriction Requirement dated Nov. 15, 2022.

U.S. Appl. No. 17/152,509, filed Jan. 19, 2021 Non-Final Office Action dated May 4, 2023.

U.S. Appl. No. 17/152,509, filed Jan. 19, 2021 Notice of Allowance dated Sep. 7, 2023.

U.S. Appl. No. 17/183,820, filed Feb. 24, 2021 Advisory Action dated Jul. 26, 2024.

U.S. Appl. No. 17/183,820, filed Feb. 24, 2021 Advisory Action dated Nov. 2, 2023.

U.S. Appl. No. 17/183,820, filed Feb. 24, 2021 Final Office Action dated May 29, 2024.

U.S. Appl. No. 17/183,820, filed Feb. 24, 2021 Final Office Action dated Sep. 28, 2023.

U.S. Appl. No. 17/183,820, filed Feb. 24, 2021 Non Final Office Action dated May 30, 2023.

U.S. Appl. No. 17/183,820, filed Feb. 24, 2021 Non-Final Office Action dated Dec. 27, 2023.

U.S. Appl. No. 17/183,820, filed Feb. 24, 2021 Notice of Allowance dated Aug. 28, 2024.

U.S. Appl. No. 17/183,820, filed Feb. 24, 2021 Restriction Requirement dated Feb. 13, 2023.

U.S. Appl. No. 17/378,304, filed Jul. 16, 2021 Non-Final Office Action dated Jun. 5, 2024.

U.S. Appl. No. 18/977,494, filed Dec. 11, 2024 Notice of Allowance dated Mar. 3, 2026.

PROXIMAL

DISTAL

STEP NEEDLE FOR INTRAOSSEOUS ACCESS DEVICE

PRIORITY

This application is a division of U.S. patent application Ser. No. 17/033,093, filed Sep. 25, 2020, now U.S. Pat. No. 12,082,843 which claims the benefit of priority to U.S. Provisional Application No. 62/907,450, filed Sep. 27, 2019, each of which is incorporated by reference in its entirety into this application.

SUMMARY

Placing an intraosseous ("I.O.") device requires driving a needle and an obturator of an access assembly through the patient's skin and tissue until the needle tip is pressed against a surface of the bone cortex. Exemplary bones which can be accessed include the proximal tibia or humerus. The needle is then drilled, using a power driver (e.g. electrical or spring), manual awl, or the like, through the outer cortex of the bone until the tip enters the medullary cavity. The user then ceases drilling, and the obturator is removed leaving the hollow needle in place. The proximal needle hub is accessed and fluids can be introduced.

Currently, the user must make a subjective assessment of when the needle is correctly placed. The user "feels" the needle advance past the relatively hard and compact, cortex layer of the bone and penetrates into the relatively soft, medullary cavity of the bone. However, the relative density of the bone cortex compared with the medullary cavity can vary depending on the bone, size of medullary space, and the patient. Accordingly, the clinician relies on a subjective assessment of a "lack of resistance" in order to determine if the medullary cavity has been successfully accessed. Further, the user relies on a subjective assessment to ensure that the needle does not advance through the medullary space and penetrate a far wall of the medullary cavity. Some devices include a stopping feature that contacts a skin surface. However, skin and subcutaneous tissue thickness can vary greatly between patients, leading to missed placements.

Briefly summarized, embodiments disclosed herein are directed to apparatus and methods for a stepped needle for an intraosseous device that uses the outer surface of the bone cortex as a reference point. Since the thickness of the bone cortex does not vary significantly between patients, the accuracy of needle placement can be improved. The device includes a needle with a stepped increase in outer diameter disposed along the needle shaft. The abrupt change in outer diameter is sufficient to provide a substantial increase in insertion force. In an embodiment, the stepped increase in outer diameter prevents the needle from being inserted any further into the bone cortex. The distance from the needle tip to the stepped increase in outer diameter is sufficient to ensure the needle tip enters the medullary cavity while preventing impingement on a far wall of the medullary cavity.

Disclosed herein is a needle assembly for an intraosseous access system including, a needle supported by a needle hub and extending to a distal tip, and a stepped increase in diameter disposed on an outer surface of the needle at a predetermined distance from the distal tip, the stepped increase in diameter configured to penetrate a skin surface and abut against a bone cortex.

In some embodiments, the predetermined distance is configured to allow the distal tip to extend through the bone cortex and into a medullary cavity of a bone. The stepped increase in diameter is formed integrally with the needle. A distal surface of the stepped increase in diameter extends perpendicular to a longitudinal axis of the needle. A distal surface of the stepped increase in diameter extends at an angle to a longitudinal axis of the needle to define a tapered shape. The needle defines a lumen having a first needle lumen diameter disposed distally of the stepped increase in diameter, and a second needle lumen diameter disposed proximally of the stepped increase in diameter, the second needle lumen diameter being larger than the first needle lumen diameter. In some embodiments, the needle assembly for an intraosseous access system further includes a third needle lumen diameter disposed proximally of the second needle lumen diameter, the third needle lumen diameter being less than the second needle lumen diameter to define a bulged portion in the needle.

In some embodiments, the needle assembly further includes an obturator disposed within the needle lumen, an outer diameter of the obturator being equal to, or less than, the first needle lumen diameter. In some embodiments, the needle assembly further includes an overtube engaged with an outer surface of the needle, a distal tip of the overtube defining a portion of the stepped increase in diameter. A longitudinal length of the overtube is less than a longitudinal length of a shaft of the needle, the overtube being adhered to the outer surface of the needle to form a collar. The overtube is slidably or rotatably engaged with the needle.

In an embodiment, the overtube includes a metal, alloy, plastic, polymer, composite, or carbon-based composite material. The overtube includes a first material, and a second material different from the first material. The first material is a relatively softer material and can elastically or plastically deform, the second material is a harder material and can be resistant to any elastic or plastic deformation. The overtube is formed of concentric tubes including a first tube formed of one of the first material or the second material and disposed adjacent the needle, and a second tube disposed on an outer surface of the first tube and formed of one of the first material or the second material. The overtube is formed of adjacent tubes including a first tube formed of the first material and disposed distally of a second tube formed of the second material. A first portion of the overtube is formed the first material and extends annularly about the needle between 1° and 359°, and a second portion of the overtube is formed of the second material and extends annularly about the needle between 1° and 359°. The distal tip of the overtube is configured to blunt and increase in diameter on contact with a surface of the bone cortex.

In some embodiments, a proximal end of the overtube abuts against the needle hub to prevent further longitudinal movement of the distal tip of the needle. A first diameter of the needle hub is between 1 cm and 3 cm. The needle hub includes a flared portion extending to a second diameter, the second diameter being greater than the first diameter. The needle hub includes a proximal housing slidably or rotatably engaged with a distal housing. In some embodiments, the needle hub includes a biasing member configured to bias the distal housing towards a proximal position relative to the proximal housing. The distal housing includes a distal face configured to engage a skin surface. The overtube is slidably engaged with the needle between a retracted position and an extended position. The distal tip of the overtube extends distally of the distal tip of the needle in the extended position. In some embodiments, the needle assembly further includes an overtube biasing member configured to bias the overtube towards the extended position. In some embodiments, the needle assembly further includes a locking mechanism configured to retain the overtube in the retracted position when in a locked configuration.

In some embodiments, the needle assembly further includes an actuator configured to transition the locking mechanism between the locked configuration and an unlocked configuration. The actuator includes rotating or sliding the proximal housing relative to the distal housing. The overtube biasing member is configured to prevent the overtube from transitioning from the extended position to the retracted position. In some embodiments, the needle assembly further includes an abutment configured to engage the overtube in the extended position and prevent the overtube transitioning from the extended position to the retracted position. In some embodiments, one of the needle or the overtube includes graduated markings.

Also disclosed is a method of accessing a medullary cavity including, penetrating a bone cortex with a distal tip of a needle, the needle including a stepped increase in outer diameter disposed at a predetermined distance from the distal tip, the predetermined distance being greater than a thickness of the bone cortex, abutting the stepped increase in outer diameter against a surface of the bone cortex to prevent further distal advancement of the distal tip, and accessing the medullary cavity.

In some embodiments, the method further includes withdrawing an obturator from a lumen of the needle until a distal tip of the obturator is proximal of a stepped increase in diameter of the lumen to allow a proximal blood flow to be observed and confirm medullary access. An overtube is slidably or rotatably engaged with the needle, a distal surface of the overtube defining a portion of the stepped increase in outer diameter. In some embodiments, the method further includes abutting a proximal end of the overtube against a needle hub to prevent further distal advancement of the distal tip of the needle. In some embodiments, the method further includes abutting a distal surface of a distal housing of a needle hub against a skin surface, the distal housing slidably or rotatably engaged with a proximal housing to allow the distal tip to continue to advance distally to access the medullary cavity. In some embodiments, the method further includes biasing the distal housing towards a distal position relative to the proximal housing.

In some embodiments, the method further includes transitioning the overtube between a retracted position, where a distal surface of the overtube is disposed at a predetermined distance from the distal tip of the needle, and an extended position where a distal surface of the overtube is disposed distally of the distal tip of the needle. In some embodiments, the method further includes biasing the overtube to the extended position. In some embodiments, the method further includes locking the overtube in the retracted position. In some embodiments, the method further includes sliding or rotating the proximal housing relative to the distal housing to unlock the overtube and transition the overtube from the retracted position to the extended position. In some embodiments, the method further includes engaging an abutment with a portion of the overtube to prevent the overtube transitioning from the extended position to the retracted position.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
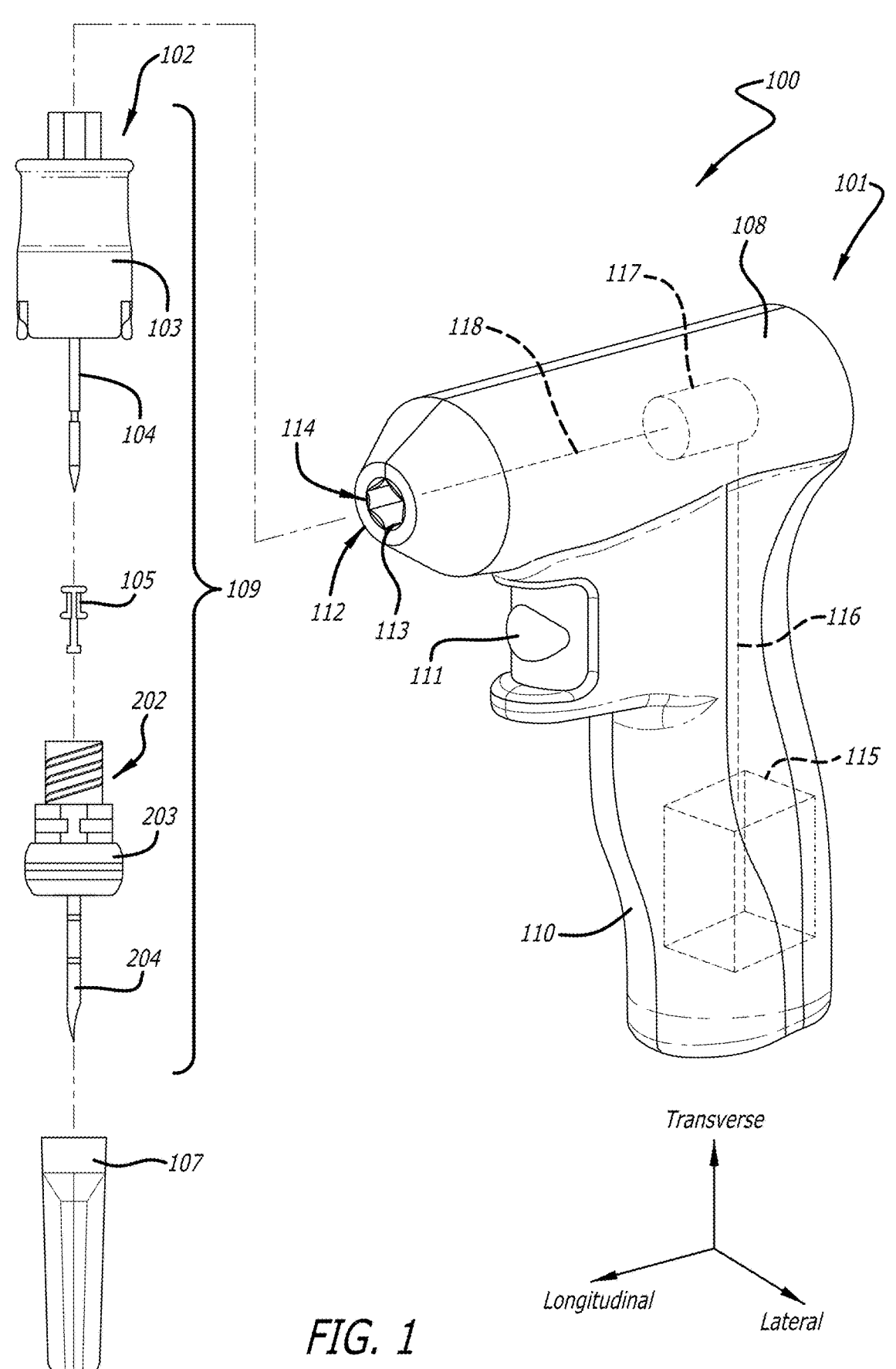
FIG. 1 illustrates an exploded view of an embodiment of an intraosseous access system, wherein an access assembly subset of the system is depicted slightly enlarged and in elevation, and an automated driver component is depicted in perspective, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

As shown in FIG. 1, and to assist in the description of embodiments described herein, a longitudinal axis extends substantially parallel to an axial length of a needle 204 extending from the driver 101. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

The present disclosure relates generally to intraosseous ("I.O.") access devices, systems, and methods thereof. FIG. 1 shows an exploded view of an exemplary embodiment of an intraosseous access system 100, with some components thereof shown in elevation and another shown in perspective. The intraosseous access system 100 can be used to penetrate skin and underlying hard bone for intraosseous access, such as, for example to access the marrow of the bone and/or a vasculature of the patient via a pathway through an interior of the bone.

In an embodiment, the system includes a driver 101 and an access assembly 109. The driver 101 can be used to rotate the access assembly 109 into a bone of a patient. In embodiments, the driver 101 can be automated or manual. In an embodiment, the driver 101 is an automated driver 108. For example, the automated driver 108 can be a drill that achieves high rotational speeds.

The intraosseous access system 100 can further include an obturator assembly 102, a shield 105, and a needle assembly 202, which may be referred to, collectively, as the access assembly 109. The access assembly 109 may also be referred to as an access system. The obturator assembly 102 is referred to as such herein for convenience. In an embodiment, the obturator assembly 102 includes an obturator 104. However, in some embodiments, the obturator 104 may be replaced with a different elongated medical instrument. As used herein, the term "elongated medical instrument" is a broad term used in its ordinary sense that includes, for example, such devices as needles, cannulas, trocars, obturators, stylets, and the like. Accordingly, the obturator assembly 102 may be referred to more generally as an elongated medical instrument assembly. In like manner, the obturator 104 may be referred to more generally as an elongated medical instrument.

In an embodiment, the obturator assembly 102 includes a coupling hub 103 that is attached to the obturator 104 in any suitable manner (e.g., one or more adhesives or overmolding). The coupling hub 103 can be configured to interface with the driver 101. The coupling hub 103 may alternatively be referred to as an obturator hub 103 or, more generally, as an elongated instrument hub 103.

In an embodiment, the shield 105 is configured to couple with the obturator 104. The coupling can permit relative longitudinal movement between the obturator 104 and the shield 105, such as sliding, translating, or other movement along an axis of elongation (i.e., axial movement), when the shield 105 is in a first operational mode, and can prevent the same variety of movement when the shield 105 is transitioned to a second operational mode. For example, as further discussed below, the shield 105 may couple with the obturator 104 in a manner that permits longitudinal translation when the obturator 104 maintains the shield 105 in an unlocked state, and when the obturator 104 is moved to a position where it no longer maintains the shield in the unlocked state, the shield 105 may automatically transition to a locked state in which little or no translational movement is permitted between the shield 105 and the obturator 104. Stated otherwise, the shield 105 may be longitudinally locked to a fixed or substantially fixed longitudinal orientation relative to the obturator 104 at which the shield 105 inhibits or prevents inadvertent contact with a distal tip of the obturator. In various embodiments, the shield 105 may be configured to rotate relative to the obturator 104 about a longitudinal axis of the obturator 104 in one or more of the unlocked or locked states.

With continued reference to FIG. 1, the needle assembly 202 is referred to as such herein for convenience. In an embodiment, the needle assembly 202 includes a needle 204. However, in various other embodiments, the needle 204 may be replaced with a different instrument, such as, for example, a cannula, a tube, or a sheath, and/or may be referred to by a different name, such as one or more of the foregoing examples. Accordingly, the needle assembly 202 may be referred to more generally as a cannula assembly or as a tube assembly. In like manner, the needle 204 may be referred to more generally as a cannula.

In an embodiment, the needle assembly 202 includes a needle hub 203 that is attached to the needle 204 in any suitable manner. The needle hub 203 can be configured to couple with the obturator hub 103 and may thereby be coupled with the driver 101, as further discussed below. The needle hub 203 may alternatively be referred to as a cannula hub 203.

In an embodiment, the shield 105 is configured to couple with the needle hub 203. The coupling can prevent relative axial or longitudinal movement between the needle hub 203 and the shield 105, such as sliding, translating, or the like, when the shield 105 is in the first operational mode, and can permit the shield 105 to decouple from the needle hub 203 when the shield 105 is transitioned to the second operational mode. For example, as further discussed below, the shield 105 may couple with the needle hub 203 so as to be maintained at a substantially fixed longitudinal position relative thereto when the obturator 104 maintains the shield 105 in the unlocked state, and when the obturator 104 is moved to a position where it no longer maintains the shield in the unlocked state, the shield 105 may automatically transition to a locked state relative to the obturator 104, in which state the shield 105 also decouples from the needle hub 203.

In an embodiment, the shield 105 can be coupled with the obturator 104, the obturator 104 can be inserted into the needle 204, and the obturator hub 103 can be coupled to the needle hub 203 to assemble the access assembly 109. In an embodiment, a cap 107 may be provided to cover at least a distal portion of the needle 204 and the obturator 104 prior to use of the access assembly 109. For example, in an embodiment, a proximal end of the cap 107 can be coupled to the obturator hub 103.

With continued reference to FIG. 1, the automated driver 108 may take any suitable form. The driver 108 may include a handle 110 that may be gripped by a single hand of a user. The driver 108 may further include an actuator 111 of any suitable variety via which a user may selectively actuate the driver 108 to effect rotation of a coupling interface 112. For example, the actuator 111 may comprise a button, as shown, or a switch or other mechanical or electrical element for actuating the driver 108. In an embodiment, the coupling interface 112 is formed as a socket 113 that defines a cavity 114. The coupling interface 112 can be configured to couple with the obturator hub 103. In an embodiment, the socket 113 includes sidewalls that substantially define a hexagonal cavity into which a hexagonal protrusion of the obturator hub 103 can be received. Other suitable connection interfaces are contemplated.

The automated driver 108 can include an energy source 115 of any suitable variety that is configured to energize the rotational movement of the coupling interface 112. For example, in some embodiments, the energy source 115 may comprise one or more batteries that provide electrical power for the automated driver 108. In other embodiments, the energy source 115 can comprise one or more springs (e.g., a coiled spring) or other biasing member that may store potential mechanical energy that may be released upon actuation of the actuator 111.

The energy source 115 may be coupled with the coupling interface 112 in any suitable manner. For example, in an embodiment, the automated driver 108 includes an electrical, mechanical, or electromechanical coupling 116 to a gear assembly 117. In some embodiments, the coupling 116 may include an electrical motor that generates mechanical movement from electrical energy provided by an electrical energy source 115. In other embodiments, the coupling 116 may include a mechanical linkage that mechanically transfers rotational energy from a mechanical (e.g., spring-based) energy source 115 to the gear assembly 117. The automated driver 108 can include a mechanical coupling 118 of any suitable variety to couple the gear assembly 117 with the coupling interface 112. In other embodiments, the gear assembly 117 may be omitted.

In embodiments, the automated driver 108 can rotate the coupling interface 112, and thereby, can rotate the access assembly 109 at rotational speeds significantly greater than can be achieved by manual rotation of the access assembly 109. For example, in various embodiments, the automated driver 108 can rotate the access assembly 109 at speeds of between 200 and 3,000 rotations per minute. However, greater or lesser rotations per minute are also contemplated.

Further details and embodiments of the intraosseous access system 100 can be found in patent application publications: WO 2018/075694, WO 2018/165334, WO 2018/165339, and US 2018/0116693, each of which is incorporated by reference in its entirety into this application.

Figure 2:
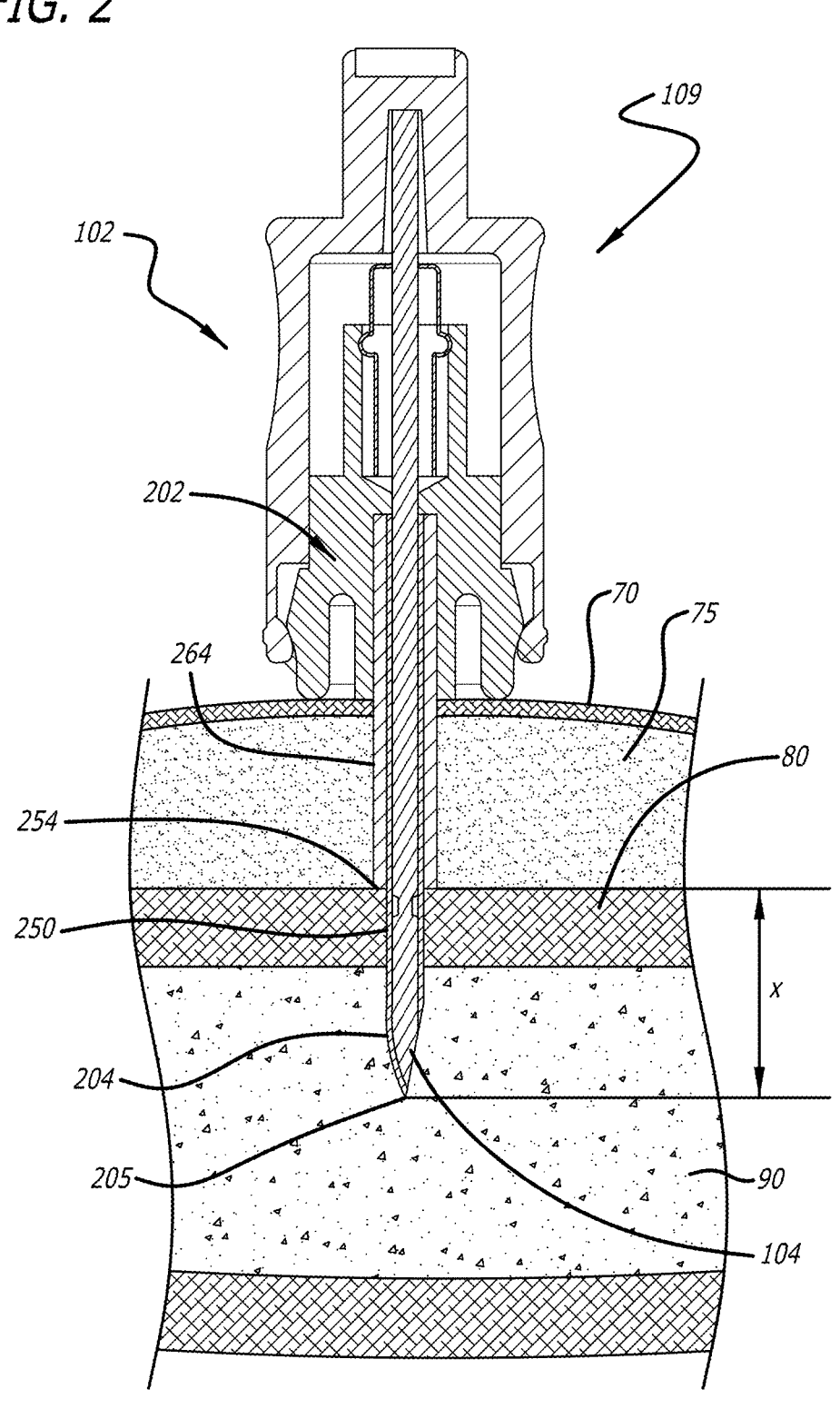
FIG. 2 illustrates the access assembly of FIG. 1 accessing a medullary cavity of a patient, in accordance with embodiments disclosed herein.

FIG. 2 shows an exemplary access assembly 109, which includes an obturator assembly 102 and a needle assembly 202. The access assembly 109 is disposed within a patient with a tip 205 of the needle 204 extending through the skin surface 70, subcutaneous tissues 75, bone cortex 80, and enters the medullary cavity 90. The needle 204 further includes an obturator 104 disposed within a lumen thereof to prevent tissue, bone fragments and the like, entering and obstructing the needle lumen.

Figure 4:
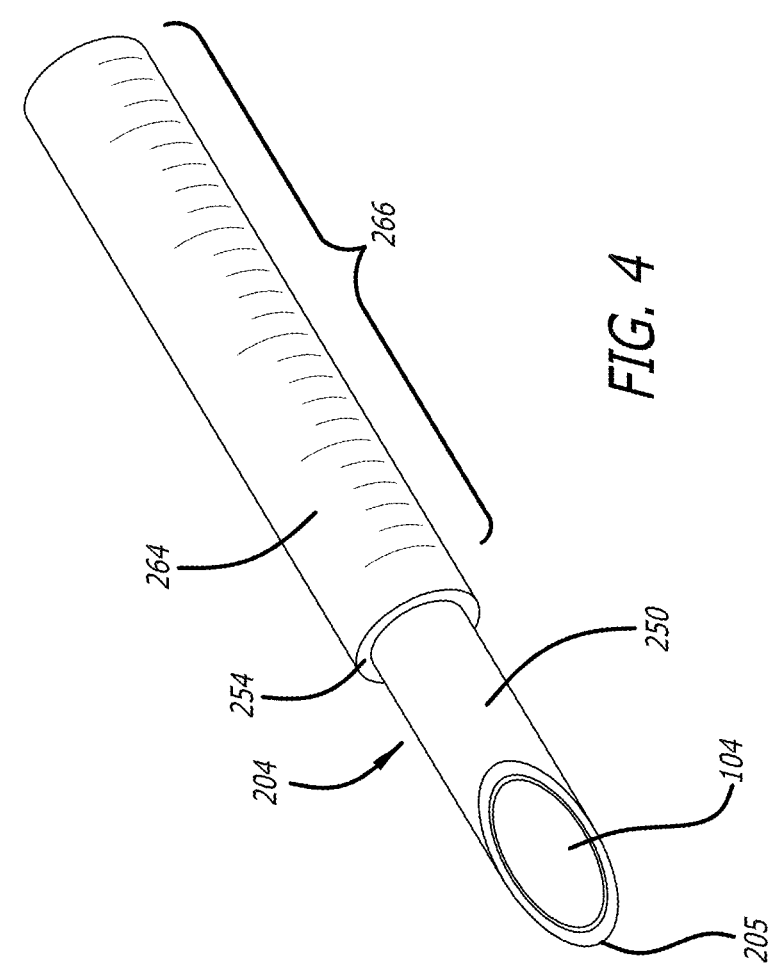
FIG. 4 illustrates a perspective view of an access assembly including a stepped portion, in accordance with embodiments disclosed herein.
Figure 3:
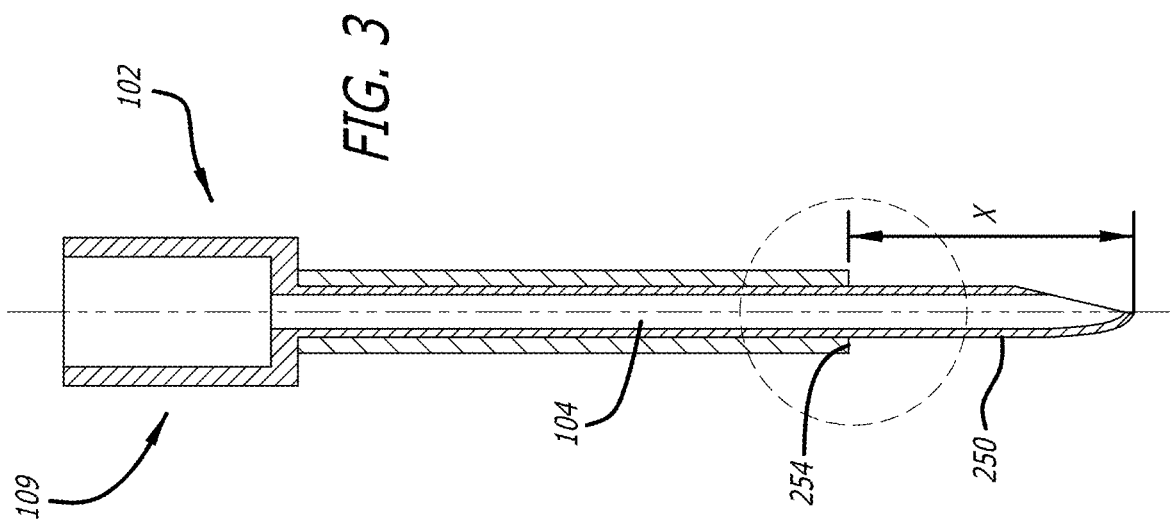
FIG. 3 illustrates a side profile view of an access assembly including a stepped portion, in accordance with embodiments disclosed herein.

As shown in FIGS. 2-4, the needle 204 further includes a stepped portion ("step") 254 disposed annularly about an outer surface of the needle shaft 250 and defining an increase in outer diameter of the needle 204. The stepped portion 254 is positioned at a predefined distance (x) from the needle tip 205. The step 254 extends radially from the needle shaft 250 to provide an increase in outer diameter of the needle shaft 250. The step 254 provides an increase in resistance as the needle 204 is driven into the bone cortex 80. In an embodiment, the step 254 provides sufficient change in resistance to indicate to a user that the step 254 has contacted the outer surface of the bone cortex 80, indicating that the needle bevel is within the medullary cavity 90, as shown in FIG. 2. In an embodiment, the step 254 prevents any further insertion of the needle 204 into the bone cortex 80. In an embodiment, as shown in FIG. 4, the needle 204 includes an overtube 264 that provides the step 254, as will be described in more detail herein.

In an embodiment, the needle 204, overtube 264, or combinations thereof, include graduated markings 266 to indicate a depth of the needle tip 205 and guide the user as to when the needle tip 205 is correctly placed. In an embodiment, the overtube 264 can be formed of a metal, alloy, plastic, polymer, composite, carbon-based composite, combinations thereof, or the like. In an embodiment, a first portion of the overtube 264 can be formed of a first material, and a second portion of the overtube 264 can be formed of a second material different from the first material. In an embodiment the first material and the second material can display different mechanical properties. In an embodiment, the first material can be formed of a metal, alloy, or the like, and the second material can be formed of a plastic, polymer, or the like.

Figure 5A:
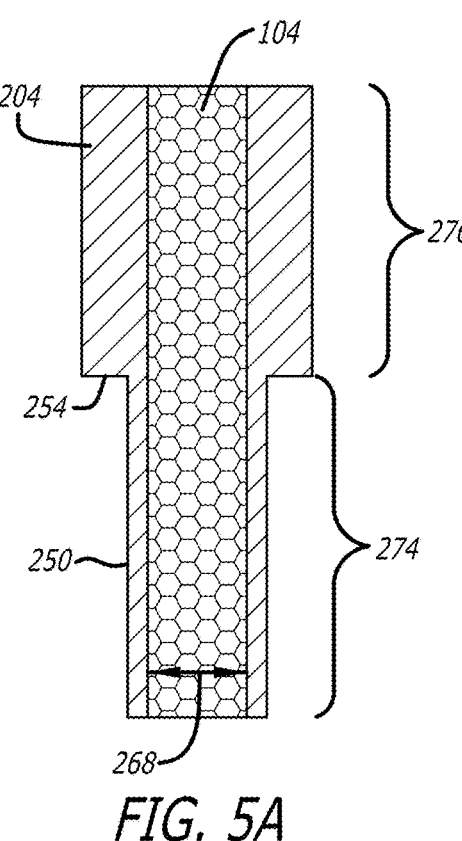
FIGS. 5A-5L illustrate cross-sectional views of a stepped portion of the access assembly, in accordance with embodiments disclosed herein.

FIGS. 5A-5H show close up views of embodiments of the step 254. It will be appreciated the features of these embodiments can be used in any combination without limitation and fall within the scope of the present invention. As shown in FIG. 5A, in an embodiment, the step 254 is formed integrally with the needle shaft 250. As such, the needle 204 includes a distal portion 274 disposed distally of the step 254 and defines a first outer diameter, and a proximal portion 276 disposed proximally of the step 254 and defining a second outer diameter. The first outer diameter being less than the second outer diameter to define the step 254. A first needle lumen diameter 268 defines a constant diameter both distally and proximally of the step 254. Accordingly, a wall thickness of the proximal portion 276 of the needle 204 is greater than a wall thickness of the distal portion 274 of the needle 204.

Figure 5B:
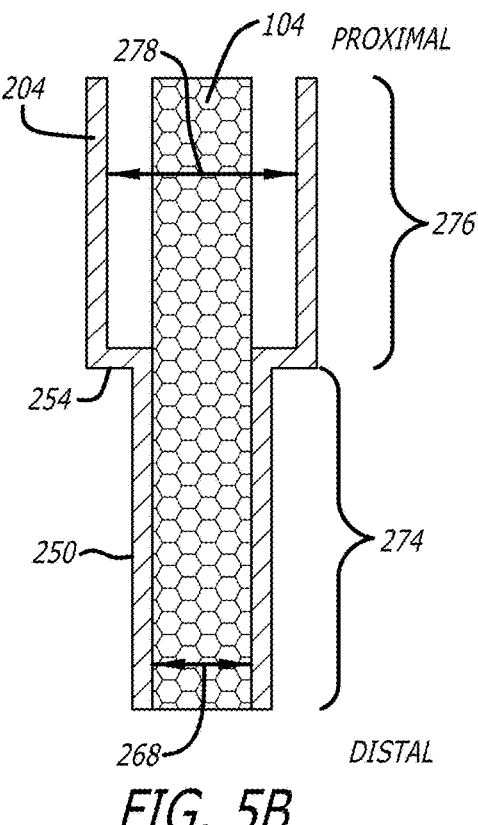

As shown in FIG. 5B, in an embodiment, the step 254 is formed integrally with the needle shaft 250. As such, the needle 204 includes a distal portion 274 disposed distally of the step 254 and defines a first outer diameter, and a proximal portion 276 disposed proximally of the step 254 and defining a second outer diameter. The first outer diameter being less than the second outer diameter to define the step 254. A needle lumen extending through the distal portion defines a first diameter 268, and a needle lumen extending through the proximal portion defines a second diameter 278, the second lumen diameter 278 being greater than the first lumen diameter 268. Accordingly, a wall thickness of the needle 204 maintains a substantially constant thickness.

Figure 5C:
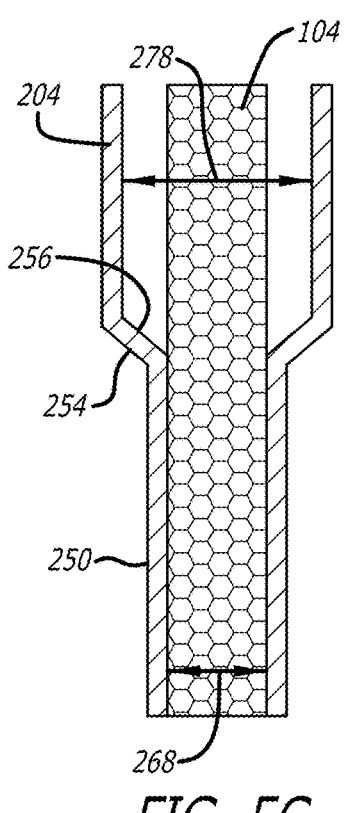

As shown in FIG. 5C, in an embodiment, the needle 204 defines a lumen including a first lumen diameter 268 and a second lumen diameter 278, and a substantially constant wall thickness, as described herein in reference to FIG. 5B. The step 254 defines a tapered outer profile to provide an increase in outer diameter and to facilitate insertion of the needle through subcutaneous tissues 75. The step 254 provides an increase in resistance when the step 254 contacts the bone cortex 80. In an embodiment, a portion of the step 254 can be inserted within the bone cortex 80. The needle lumen also includes a tapered transition portion 256, adjacent the step 254 and disposed between the distal portion 274 of the needle 204, which defines a first lumen diameter 268, and the proximal portion 276 of the needle 204, which defines a second lumen diameter 278.

In an embodiment, the needle 204 can include a third portion (not shown) disposed proximally of the proximal portion 276 that defines a needle lumen having a first diameter 268, i.e. a needle lumen that is less that the second lumen diameter 278. As such the proximal portion 276 defines a "bulged" portion disposed at a predetermined distance (x) from the needle tip, as described herein. In an embodiment, the predetermined distance (x) can be between 1 cm and 3 cm, however other predetermined distances are also possible and within the scope of the invention. In an embodiment, the bulged proximal portion 276 can include a stepped, tapered, or rounded increase in diameter and decrease in diameter, back to the diameter of the distal portion 274.

Figure 5D:
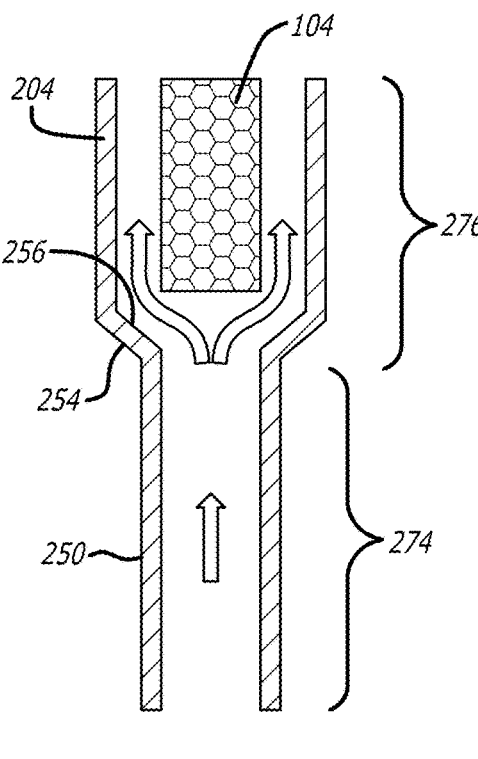

In the embodiments shown in FIGS. 5B and 5C, the needle lumen facilitates medullary cavity access confirmation. In use, the needle 204 is inserted through the bone cortex 80 until the step 254 increases resistance. A user can then confirm the needle bevel is disposed within the medullary cavity by partially withdrawing the obturator 104 until a distal end thereof is proximal of the step 254. As shown in FIG. 5D, blood can then flow proximally through the needle lumen, past the obturator 104, to a needle hub where the blood flow can be observed to confirm medullary cavity access. If the needle tip 205 has not accessed the medullary cavity 90, a reduced or absent blood flow will be observed. In which case the obturator 104 can be reinserted with minimal risk of contamination, and insertion of the access assembly 109 can continue through the bone cortex 80. In an embodiment, the tapered transition portion 256 of the needle lumen can facilitate reinsertion of the obturator 104 within the distal portion of the needle lumen.

Figure 5E:
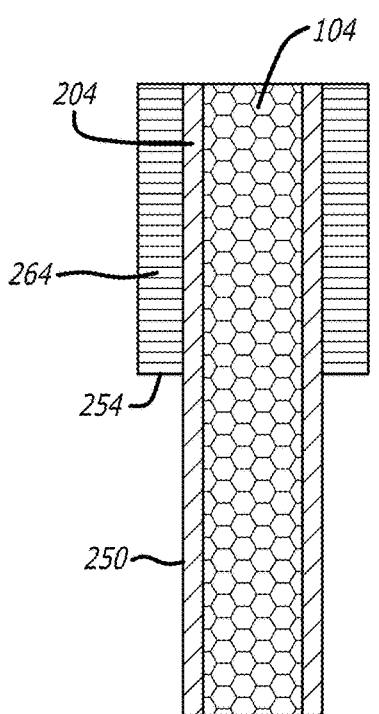
Figure 5F:
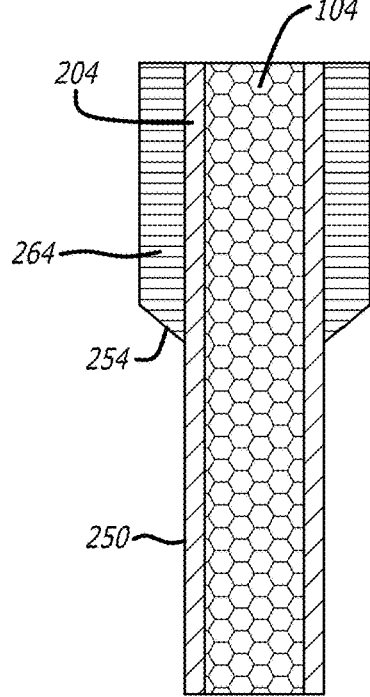

As shown in FIGS. 5E-5F, in an embodiment, the needle 204 defines a substantially constant outer diameter, a constant wall thickness, and a constant lumen diameter. The needle 204 further includes an overtube 264 disposed on an outer surface of the needle 204 and defines an overtube wall thickness that defines the step 254. In an embodiment, a distal end of the overtube 264 extends to a point that is proximal of the needle tip 205. In an embodiment, a distal end of the overtube 264 extends to a point that is a predetermined distance (x) from the needle tip 205. As noted, the predetermined distance (x) can be between 1 cm and 3 cm, however other predetermined distances are also possible and within the scope of the invention, as described herein. As shown in FIG. 5F, the distal end of the overtube 264 can be tapered to facilitate insertion of the needle through tissues 70, 75.

In an embodiment, the overtube 264 is attached to the needle shaft by adhesive, welding, bonding, crimping or the like. Accordingly, the overtube 264 is fixed and unable to move relative to the needle 204. In an embodiment, the overtube 264 can extend over a portion of the needle 204. In an embodiment, a proximal end of the overtube 264 can extend to a point that is distal of the needle hub 203. In an embodiment, the overtube 264 can define a collar that is attached to the needle shaft as described herein.

In an embodiment, the overtube 264 is slidably engaged with the needle 204 and can be selectively secured in place. The position of a distal end of the overtube 264 can be adjusted relative to the needle tip 205 to a preferred distance along the longitudinal axis. The user can select a predetermined distance (x) depending on the type of target bone, the procedure, or age or health of the patient, or the like. For example, a predetermined distance (x) of 10 mm-15 mm would be preferable for smaller, pediatric patients, where a distance of 15 mm-30 mm would be preferable for larger, adult patients.

In an embodiment, the overtube 264 is rotatably engaged with the needle 204 about the longitudinal axis. This allows the needle 204 to spin freely while the overtube 264 remains substantially stationary. In an embodiment, the needle 204 can be drilled through the bone cortex 80 and the overtube 264 protects the surrounding tissues 70, 75 from twisting about the needle 204 as the needle spins. The overtube 264 therefore protects the tissues 70, 75 from damage and irritation. In an embodiment, the overtube 264 can be both slidably and rotatably engaged with the needle 204. Accordingly, the user can select a predetermined distance (x) between the distal end of the overtube 264 and the needle tip 205. Further the overtube can protect any surrounding tissue 70, 75 as the needle is drilled into the bone cortex 80.

Figure 5G:
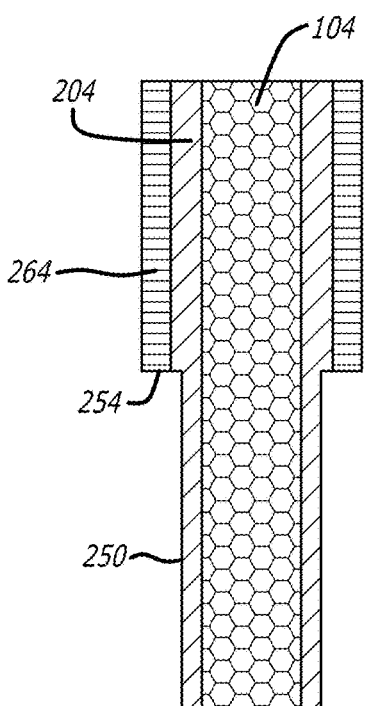
Figure 5H:
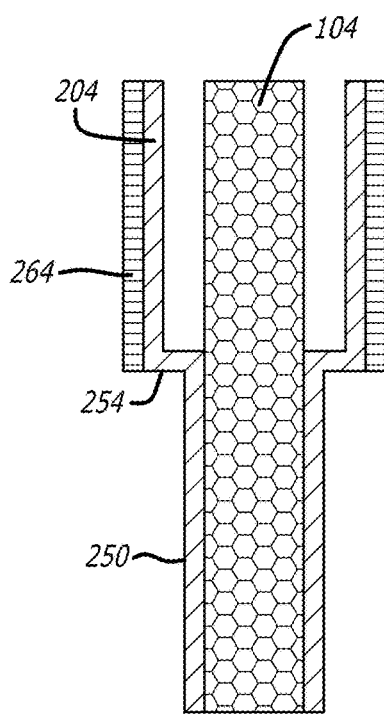

In an embodiment, as shown in FIGS. 5G and 5H, the needle 204 includes both a stepped portion 254, for example as described herein in reference to FIGS. 5A-5D, as well as an overtube 264. The distal end of the overtube 264 can align with the stepped portion 264. In an embodiment, the distal end of the overtube 264 can be positioned proximally of the stepped portion 254 to provide a second step (not shown). For example, the first step 254 can indicate that the user is approaching the predetermined depth. A user can then continue to insert the access assembly 109, including the first step, through the bone cortex 80, until a second step (not shown) contacts the bone cortex indicating that the desired depth is reached, or preventing any further insertion of the access assembly 109.

Figure 5I:
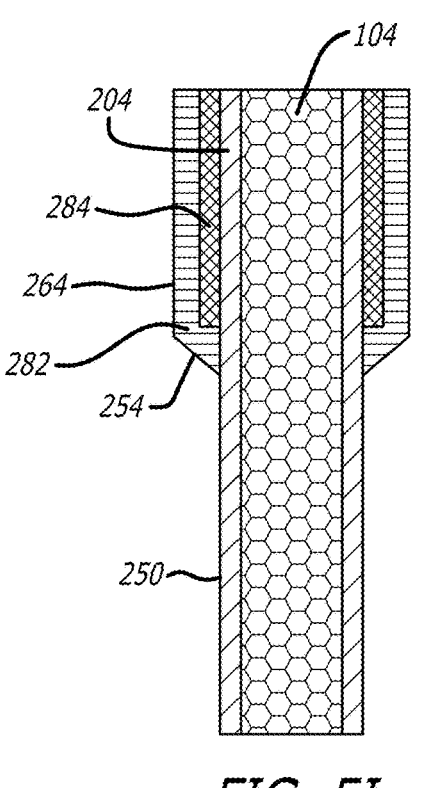
Figure 5J:
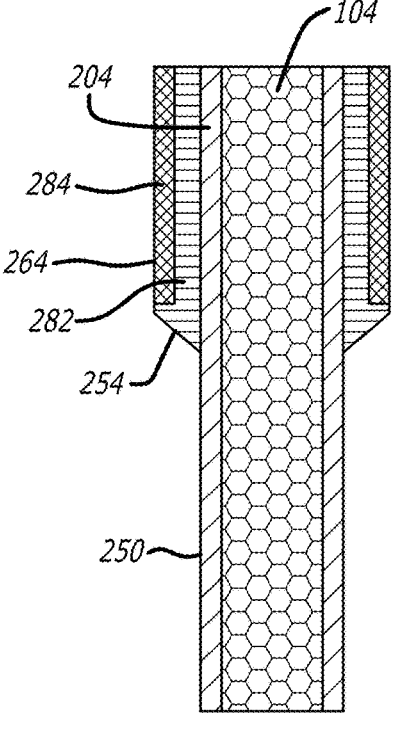

As shown in FIGS. 5I-5L, the overtube 264 can include a first material 282 and a second material 284. In an embodiment, the overtube 264 can be formed of one or more concentric tubes of one or more different materials, e.g. as shown in FIGS. 5I-5J. In an embodiment, the overtube 264 can be formed of one or more adjacent tubes of one or more different materials, disposed along the longitudinal axis, e.g. FIG. 5K. In an embodiment, the overtube 264 can include different adjacent portions formed of one or more materials.

As shown in FIGS. 5I-5J, in an embodiment, the first material is overmolded on to the second material 284, which is disposed adjacent the needle shaft 250, forming a tube thereabout. In an embodiment the first material 282 can be a plastic, polymer, or the like and the second material 284 can be a metal, alloy, or the like. In an embodiment, the first material 282 can display softer material properties or can elastically or plastically deform. In an embodiment, the second material 284 can display harder or resilient material properties and can be resistant to any elastic or plastic deformation. In an embodiment, as shown in FIG. 5J, the tube of a first material 282 can be disposed adjacent the needle shaft 250 and a tube of the second material 284 can be disposed thereover, substantially along an outer surface of the overtube 264.

In an embodiment, the second material 284 can provide structural support to overtube while the first material 282 can deform to increase the outer diameter of the overtube as it is urged against the bone cortex 80. To note the first material 282 can be sufficiently resilient to penetrate the skin surface tissues 70, 75 without deforming but can deform slightly, when urged against the bone cortex 80. Further, the relatively softer first material 282 can be configured to mitigate trauma to the bone cortex 80 as the needle 204 is rotated.

In an embodiment, a distal tip of the overtube 264, forming the stepped increase in diameter 254 can be formed of the first, relatively softer material 282. The tapered shape can facilitate penetrating the skin surface tissues 70, 75. Then, when the tapered stepped increase in diameter 254 contacts the relatively hard bone cortex 80, the tapered shape can deform and "mushroom" out, to abut against the bone cortex and provide an increase in resistance to distal advancement, as described herein. In an embodiment, the distal tip can mushroom out to a diameter that is greater than the outer diameter of the overtube 264 to provide a greater resistance to further distal advancement.

Figure 5K:
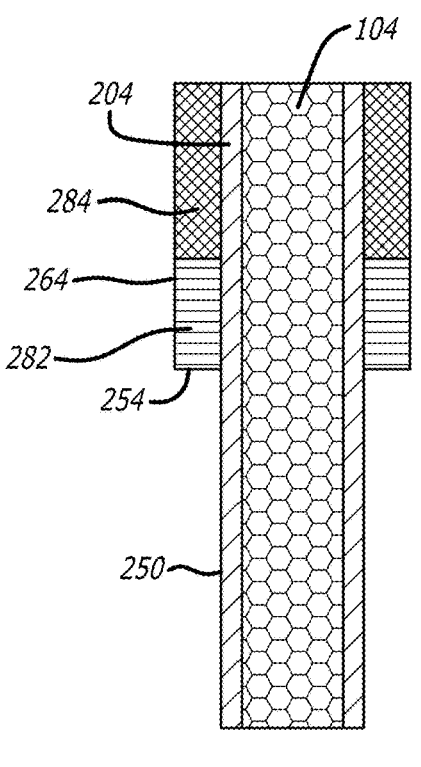
Figure 5K:
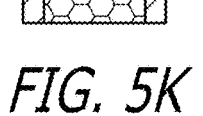

In an embodiment, as shown in FIG. 5K, the overtube 264 can be formed of one or more adjacent tubes of one or more different materials, disposed along the longitudinal axis. For example, the overtube 264 can be formed of a second, relatively harder material 284 and include a first, relatively softer material 282 disposed at a distal tip and forming the stepped increase in diameter 254. In an embodiment, the distal tip formed of the first material 282 can define a stepped increase in diameter 254 extending perpendicular to the longitudinal axis, or can define a tapered stepped increase in diameter 254, as described herein. The distal tip formed of the first material 282 can mitigate trauma to the bone cortex 80 as the overtube 264 is urged distally. In an embodiment, the distal tip formed of the first material 282 can deform, blunt, or "mushroom," to provide an increase in outer diameter, an increase resistance to further distal advancement, cushion the impact of the overtube 264 against the bone cortex, or combinations thereof.

Figure 5L:
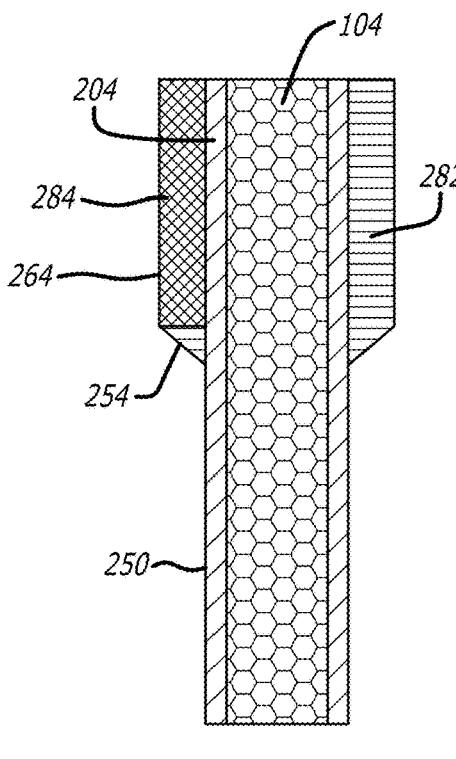

In an embodiment, as shown in FIG. 5L, a first side wall portion of the overtube 264 can be formed of a first material 282 and a second side wall portion of the overtube 264 can be formed of a second material 284. In an embodiment, each of the first side wall portion or the second side wall portion can extend along a longitudinal length of the overtube 264 from a proximal end 280 to the distal end, adjacent the stepped increase in diameter 254. In an embodiment, one of the first side wall portion or the second side wall portion can extend about the longitudinal axis between 1° and 360°. However, greater or lesser degrees are also contemplated. In an embodiment, the overtube 264 can be formed of a first half, extending about the longitudinal axis of the needle 204 by 180° and formed of a first material 282, a second half, extending about the longitudinal axis of the needle 204 by 180° and formed of a second material 284.

In an embodiment, the overtube 264 can be formed of a first quarter extending about the longitudinal axis of the needle 204 by 90° and formed of a first material 282, a second quarter disposed adjacent the first quarter, extending about the longitudinal axis of the needle 204 by 90° and formed of a second material 284, a third quarter disposed adjacent the second quarter, and extending about the longitudinal axis of the needle 204 by 90° and formed of a first material 282, and a fourth quarter disposed adjacent the third quarter, and extending about the longitudinal axis of the needle 204 by 90° and formed of a first material 282. It will be appreciated however, that other combinations of materials, and annular extensions, i.e. between 1° and 360°, of the different portions of the overtube 264 are also contemplated. In an embodiment, the overtube 264 can include a distal tip portion extending annularly about the needle 204 and formed of the first material 282. The distal tip portion can be configured to deform when contacting the bone cortex, as described herein.

Figure 6B:
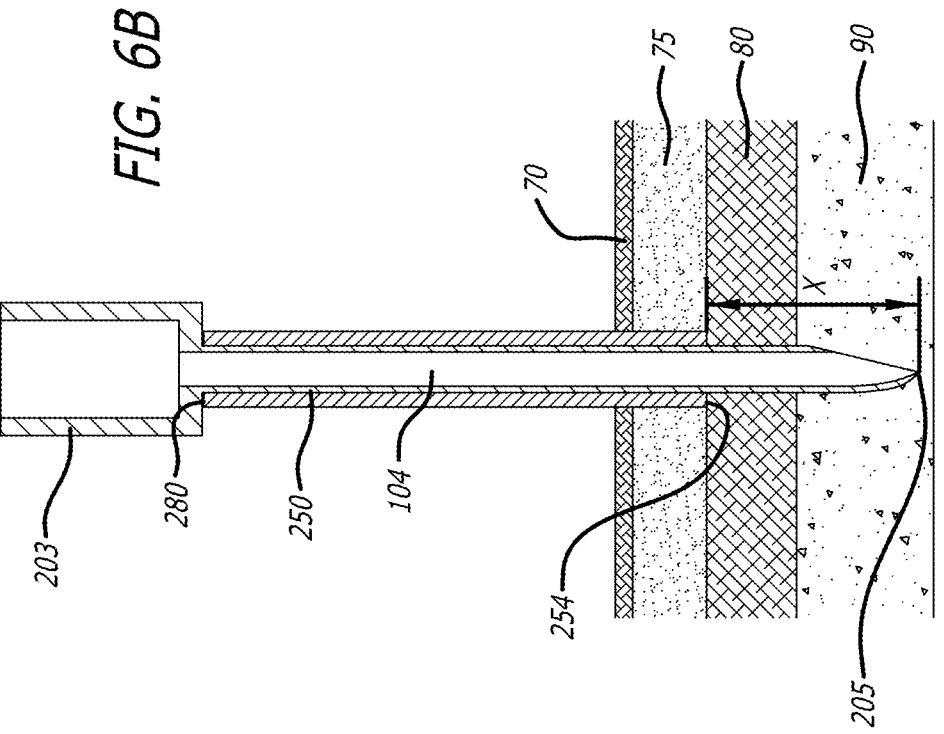
FIGS. 6A-6B illustrate cross-sectional views of an access assembly, in accordance with embodiments disclosed herein.
Figure 6A:
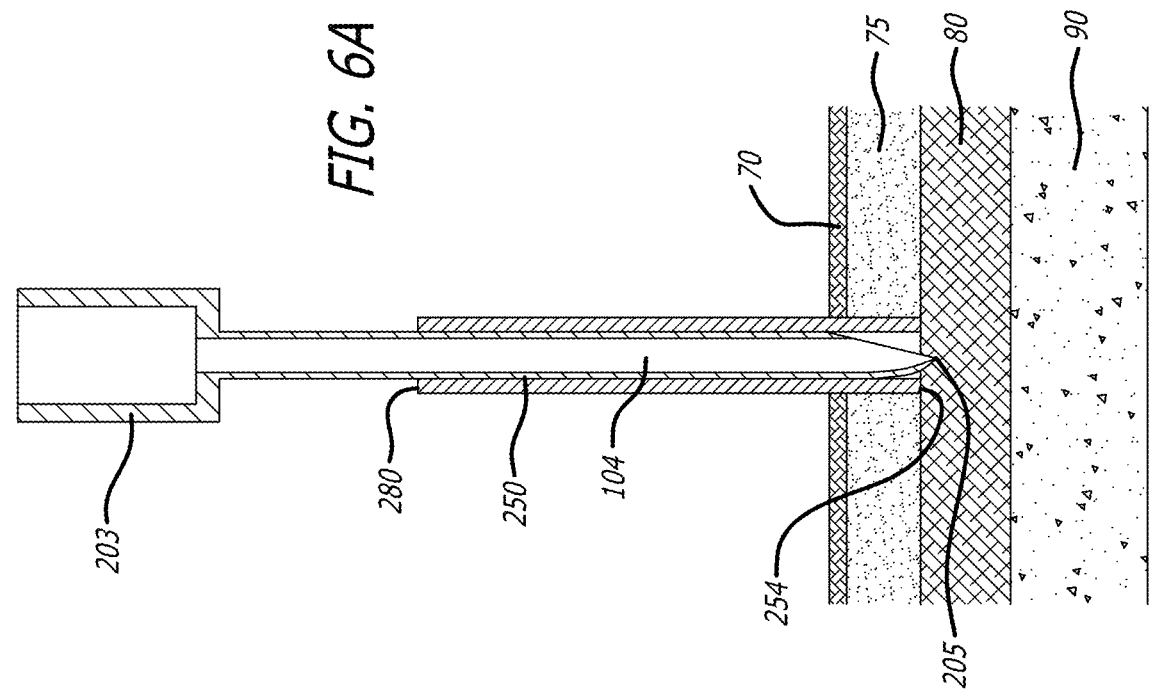

In an embodiment, as shown in FIGS. 6A-6B, the overtube 264 can be both slidably and rotatably engaged as described herein. The distal end of the overtube 264 can longitudinally align with one of the needle tip 205, the needle bevel, or a proximal edge of the needle bevel. The overtube 264 and needle 204 can then be inserted through the skin 70 and subcutaneous tissues 75 until the distal end of the overtube 264 contacts a surface of the bone cortex 80. The needle 204 can then be rotated and drilled into the bone cortex 80 while the overtube 264 can remain substantially stationary, and protects the surrounding tissues 70, 75 from twisting about needle 204 as it spins. Advantageously, the overtube 264 being rotatably engaged with the needle 204 can allow the needle to rotate freely, while the overtube 264, or more specifically, the stepped increase in diameter 254 remains substantially stationary against the surface of the bone cortex 80. This can mitigate any friction or trauma of the bone cortex 80 by mitigating any movement of stepped increase in diameter 254 relative to the surface of the bone cortex 80. The needle 204 then advances distally, through the over tube 264 and through the bone cortex 80, until a proximal end 280 of the overtube 264 contacts a needle hub 203, preventing any further advancement of the needle 204 relative to the overtube 264. It will be appreciated that when the proximal end 280 of the overtube 264 contacts the needle hub 203, the distal end of the overtube 264 will be at a predetermined distance (x) from the needle tip 205. The predetermined distance (x) being sufficient to allow the needle bevel to enter the medullary cavity 90, without the needle tip 205 contacting a far wall of the medullary cavity 90.

With continuing reference to FIGS. 6A-6B, in an embodiment, when the needle is to be removed, the needle 204 can be retracted through the bone cortex 80 and into the overtube 264 such that a needle tip 205 is disposed within the lumen of the overtube 264. Optionally, the needle 204 and overtube 264 can then be locked in place relative to each other when the needle tip 205 is disposed within the lumen of the overtube 264. The needle 204 and overtube 264 can then be withdrawn from the tissues 70, 75. Accordingly, the overtube 264 provides a safety cover for the needle 204, preventing accidental needle stick injuries once the needle is removed from the patient.

Figure 7B:
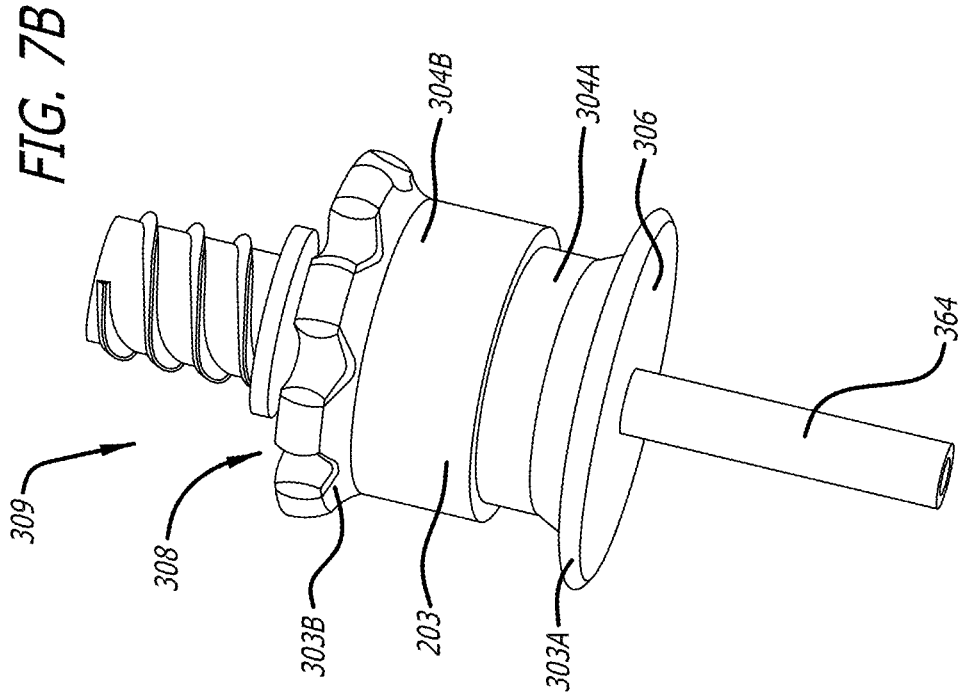
FIGS. 7A-7B illustrate perspective views of an access assembly, in accordance with embodiments disclosed herein.
Figure 7A:
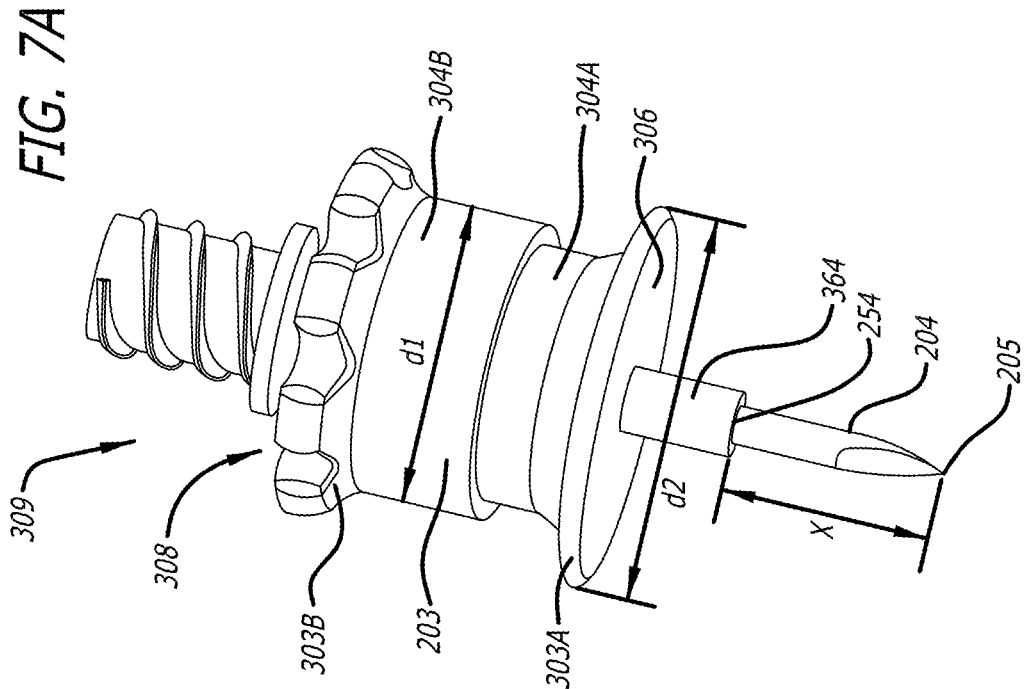

As shown in FIGS. 7A-7B, in an embodiment, an access assembly 309 can include a needle hub 203 that defines an increased diameter (d1), extending perpendicular to a longitudinal axis of the needle 204. In an embodiment, a diameter (d1) of the needle hub 203 can be between 1 cm and 3 cm although greater or lesser diameters are also contemplated. Advantageously, the needle hub 203 with the increased diameter (d1) can provide increased leverage for a user to grasp the needle hub 203 and urge the needle 204 through the bone cortex 80 by hand, or remove the needle assembly 202 by hand after the procedure is complete. The increased hub diameter can be of importance if the driver 101 fails to operate, runs out of power, or if the user is able to determine access to medullary cavity 90 more accurately by urging the needle 204 by hand, through a remaining distance of bone cortex. For example, a user may use the driver 101 to drill the needle 204 through a majority of the bone cortex 80 and then detach the access assembly 109 and drive the needle 204 the remainder of the distance by hand in order to "feel" medullary cavity access more accurately. Further, the increased hub diameter can be important to allow a user to remove the needle 204 from the bone cortex 80 without having to attach a secondary device, e.g. syringe, hemostats, or the like, to the needle hub 203 to facilitate removal of the needle 204.

In an embodiment, the needle hub 203 can include one or more flared portions 303, for example a distal flared portion 303A and a proximal flared portion 303B. The flared portion 303 can extend annularly about the hub and provide an increased diameter (d2) relative to the diameter (d1) of the needle hub 203. Advantageously, the flared portion 303 can provide support for a user when urging the needle hub 203 along the longitudinal axis in either of the proximal or distal directions. Further the flared portion 303 can guide a user's fingers towards a longitudinal midpoint of the needle hub 203 and provide a secure grasp of the needle hub 203. This can be important in an emergency situations, where a user, who is often wearing gloves, would need to grasp the hub 203 rapidly and apply significant force to the needle hub 203, while avoiding slipping.

In an embodiment, the needle hub 203 can include a distal housing 304A and a proximal housing 304B that are slidable engaged with each other, for example, in a telescoping manner. As shown in FIG. 7A, an outer diameter of the proximal housing 304A can be equal to an inner diameter of the proximal housing 304B to allow the distal housing 304A to slide into a cavity defined by the proximal housing 304B. It will be appreciated that other configurations of housings 304A, 304B are also contemplated, for example the proximal housing 304B being received within the distal housing 304A.

Advantageously, the proximal housing 304B can spin about the longitudinal axis independently of the distal housing 304A. As such, as the access assembly 309 advances into the patient, a distal face 306 of the distal housing 304A can contact a skin surface of the patient. The distal face 306 of the distal housing 304A can rest in a substantially stationary position against the skin surface, allowing the proximal housing 304B and/or needle 204 to rotate about the longitudinal axis until the medullary cavity is accessed. The distal housing 304A can mitigate friction between the access assembly 309 and the skin surface, preventing friction burns, or similar trauma.

In an embodiment, the distal housing 304A can slide independently of the proximal housing 304B and/or needle 204, along the longitudinal axis. In an embodiment, the needle hub 204 can further include a biasing member, e.g. compression spring, or the like, configured to bias the distal housing 304A towards a longitudinally distal position. In an embodiment, when a distal face 306 of the distal housing 304A contacts a skin surface of the patient, the proximal housing 304B and/or the needle 204 can continue to advance distally, along the longitudinal axis until the medullary cavity 90 is accessed. The distal housing 304A can rest on a skin surface and remain substantially stationary preventing compression or trauma of the surface tissues 70, 75 disposed between the distal face 306 and the bone cortex 80. This can be important where a thickness of the surface tissues 70, 75 can vary significantly between different patients.

Further, the distal face 306 can align with the skin surface 70 to stabilize the needle assembly 202 once the needle 204 has been placed correctly. In an embodiment, a stabilizing device can be attached to the needle hub 203 or distal housing 304A to further stabilize the needle assembly 202 relative to the skin surface 70. The biasing member disposed within the needle hub can be configured to apply sufficient pressure to the distal housing 304A to urge the distal face 306 against the skin surface 70 and stabilize the needle hub 204, without compressing the surface tissues 70, 75 between the distal face 306 and the bone cortex 80. In an embodiment, the distal face 306 can include an adhesive or the like to further stabilize the needle assembly 202 with the skin surface 70.

As shown in FIGS. 8A-8D, in an embodiment, the access assembly 309 can include an overtube 364 slidably engaged with an outer surface of the needle 204 and defining a thickness to define a stepped portion 254 at a distal end thereof. To note, the overtube 364 can allow the needle 204 to rotate independently of the overtube 364, as described herein. In an embodiment, the overtube 364 can be slidable along a longitudinal axis of the needle 204 between a retracted position (FIG. 7A) and an extended position (FIG. 7B).

In an embodiment, with the overtube 364 in the retracted position, a predetermined distance (x) between a distal tip of the overtube 364 that defines a stepped outer diameter 254 and a distal tip of the needle 205 can be sufficient to allow a bevel of the needle to access the medullary cavity 90. In the extended position, a distal tip of the overtube 364 can extend distally of the distal tip 205 of the needle 204. The needle hub 203 can include an overtube biasing member 366, e.g. a compression spring or the like, configured to bias the overtube 364 towards an extended position.

The needle hub 203 can further include a locking mechanism 340 configured to selectively retain the overtube 364 in a retracted position. As shown, the locking mechanism is disposed at a mid-section of the overtube 364, however, it will be appreciated that other configurations of locking mechanism 340 are also contemplated including disposing towards a proximal end. In the retracted position, the locking mechanism 340 can inhibit proximal movement of the overtube 364 relative to the needle 204 to maintain the predetermined distance (x) between the stepped portion 254 and the needle tip 205. Further, the locking mechanism in the locked configuration, can retain the overtube 364 to prevent distal advancement of the overtube 364 relative to the needle 204. In an embodiment, the locking mechanism 340 can be transitioned from the locked configuration to the unlocked configuration to allow the overtube biasing member 366 to urge the overtube 364 to the extended position. Advantageously, in the extended position, the overtube 364 can prevent accidental needle stick injuries when the needle 204 is withdrawn proximally from the patient.

In an embodiment, the locking mechanism 340 can be transitioned from the locked configuration to the unlocked configuration by rotating the proximal housing 304B relative to the distal housing 304A in one of a clockwise or anti-clockwise direction. Advantageously, the proximal housing 304B can include a gripping feature 308 configured to facilitate grasping the proximal housing 304B and rotating the proximal housing about the longitudinal axis. Exemplary gripping features 308 can include grooves, ridges, or similar structures, and/or can include different materials disposed on a surface of the proximal housing 304B that have an increased friction co-efficient, e.g. rubber, silicone, or the like, or combinations thereof. As shown, the gripping feature 308 is disposed on a flared portion 303B of the proximal housing 304B, however other configurations of gripping features are also contemplated. Often a user can be wearing gloves when manipulating the needle hub 203 and the increased diameter (d1) of the needle hub 203, the flared portion(s) 303, and/or gripping feature(s) 308 can facilitate manipulation of the needle hub 203 even with gloves on.

In an embodiment, the locking mechanism 340 can be transitioned from the locked configuration to the unlocked configuration by sliding the proximal housing 304B relative to the distal housing 304A, along a longitudinal axis. For example, a user can grasp the proximal housing 304B and slide proximally away from the distal housing along the longitudinal housing to activate one or more cantilever systems that can transition the locking mechanism from the locked configuration to the unlocked configuration. In the unlocked configuration the biasing member 366 can urge the overtube 364 distally to the extended position, as described herein. As will be appreciated, the distal flared portion 303A and the proximal flared portion 303B can facilitate grasping the respective distal housing 304A and proximal housing 304B and sliding longitudinally apart, as described herein.

Figure 8B:
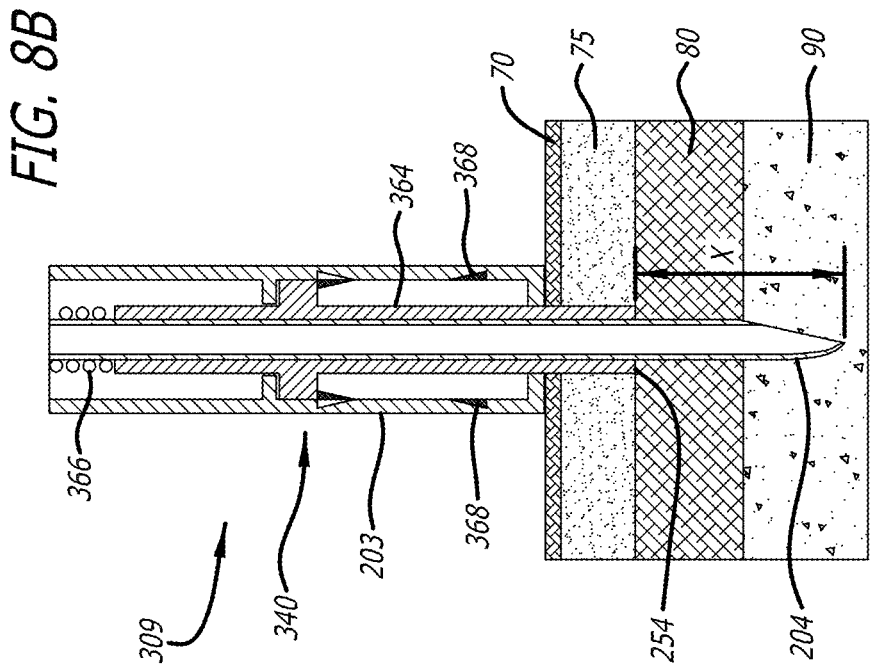
FIGS. 8A-8D illustrate cross-sectional views of an access assembly, in accordance with embodiments disclosed herein.
Figure 8A:
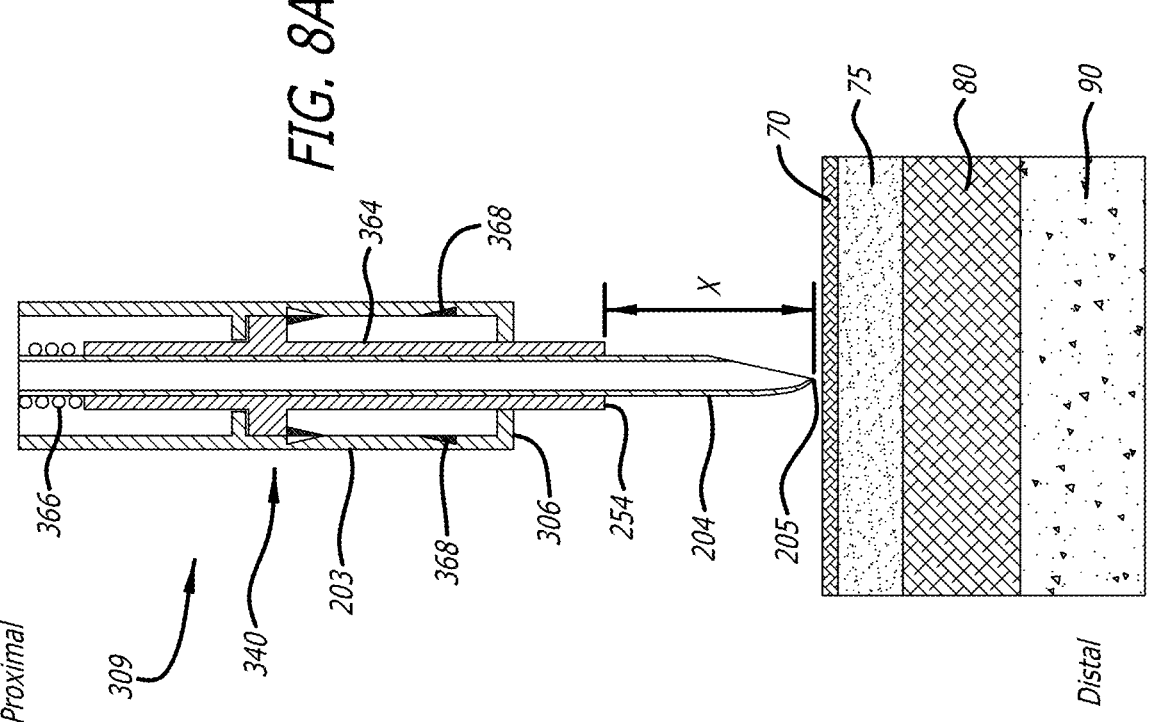
Figure 8D:
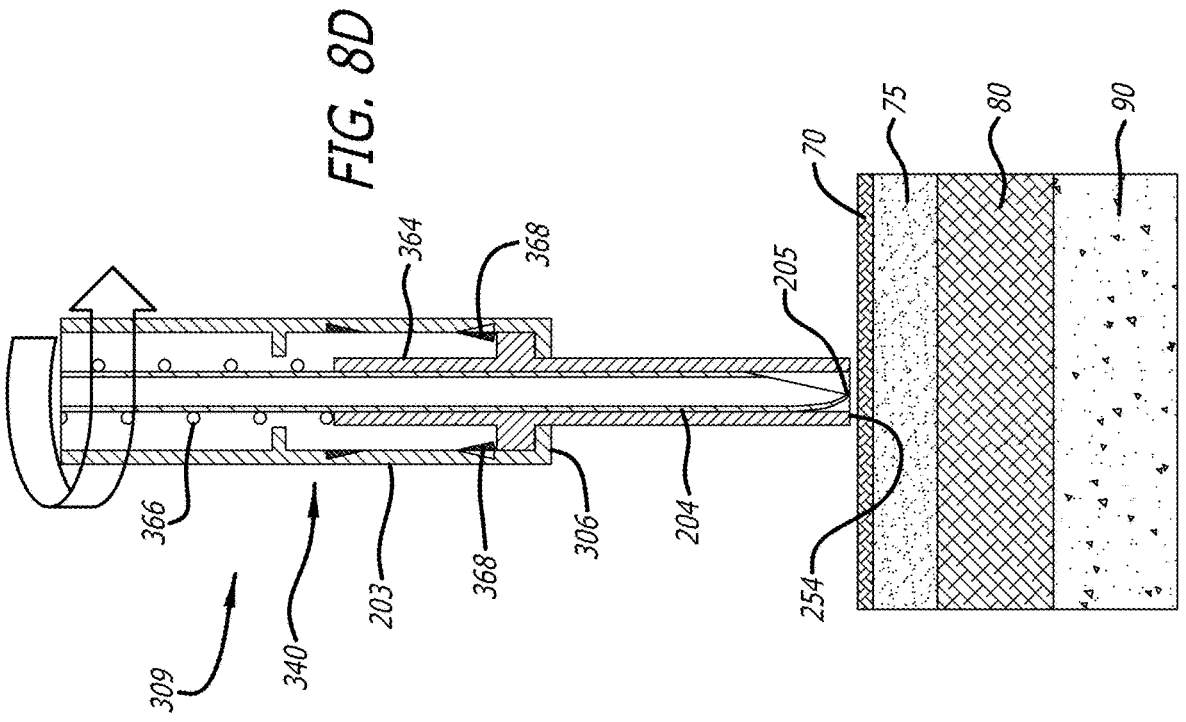

As shown in FIG. 8D, in an embodiment, the biasing member 366 is configured to prevent proximal movement of the overtube 364 from the extended position to prevent retraction of the overtube 364 and prevent accidental needle stick injuries. In an embodiment, the needle hub 203 can include an abutment 368 configured to abut against the overtube 364, or portion thereof, to prevent proximal movement of the overtube 364 from the extended position to prevent retraction of the overtube 364 and prevent accidental needle stick injuries.

In an exemplary method of use, as shown in FIGS. 7A-8D, an access assembly 309 can be provided, as described herein. The access assembly 309 can be coupled with an intraosseous access system 100, configured to drive the needle 204 through a bone cortex 80 and access a medullary cavity 90.

As shown in FIG. 8A, prior to insertion of the needle 204, the access assembly 309 can include an overtube 364 disposed in the retracted position and retained in the retracted position by the locking mechanism 340. As shown in FIG. 8B, the access assembly can be rotated by the driver 101 to drill the needle 204 through the skin 70 and surface tissues 75 to the bone cortex 80. The driver 101 can continue to drill the needle 204 through the bone cortex 80 and a distal portion of the overtube 364 can be inserted through the skin 70 and surface tissues 75 until the stepped portion 254 abuts against a surface of the bone cortex 80, preventing any further distal movement of the access assembly 309.

In an embodiment, prior to insertion of the needle 204, the overtube 364 can be biased towards the extended position. The needle 204 and overtube 364 can be advanced through the surface tissues 70, 75 until a distal tip of the overtube 364 contacts the bone cortex 80. The driver 101 can be activated to drill the needle 204 through the bone cortex 80. As the needle 204 advances, the overtube 364 can transition towards the retracted position.

In an embodiment, the distal surface 306 of the needle hub 203 can abut against the skin surface. As noted, the distal housing 304A can be configured to contact the skin surface and remain substantially stationary while allowing the needle 204 and/or proximal housing 304B to continue to rotate. Advantageously, then distal housing 308A can prevent friction burns, or similar trauma between the needle hub 203 and the skin surface 70.

In an embodiment, the distal surface 306 can contact the skin surface 70 prior to the stepped portion 254 contacting the bone cortex 80, or prior to the overtube 364 fully transitioning to the retracted position. As noted, the distal housing 304A can be slidably engaged with the needle hub 203 and configured to allow the needle 204 to continue to advance distally while the distal housing 304A rests on a skin surface 70. Advantageously, this can prevent the soft tissues 70, 75 from being compressed between the distal face 306 and the bone cortex 80 and stabilizes the needle hub 203 with the skin surface 70. In an embodiment, the distal housing 304A configured as such, can allow a stabilizing device to be attached to the needle hub 203 or the distal housing 304A to further stabilize the needle assembly 202 relative to the skin surface 70. Optionally, when the overtube 364 has fully transitioned to the retracted configuration, the locking mechanism can be configured to automatically retain the overtube 364 in the retracted position.

Figure 8C:
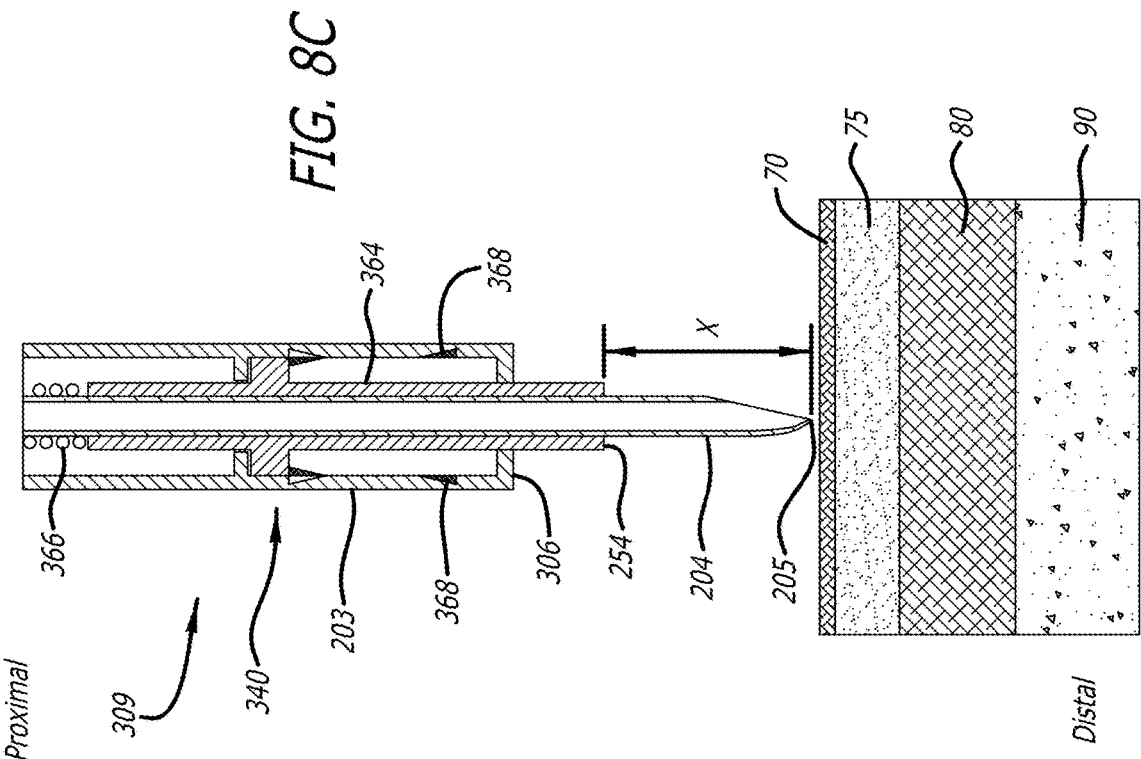

As shown in FIGS. 8C-8D, once the medullary cavity 90 has been accessed and the procedure is complete, the needle assembly 202 can be withdrawn proximally. Prior to removal of the needle 204, or after removal of the needle 204 from the insertion site, the needle hub 203 can be actuated to transition a locking mechanism 340 from the lock configuration to the unlocked configuration. In an embodiment, the proximal housing 304B can be rotated either clockwise or anticlockwise relative to the distal housing 304A to actuate the needle hub 203. In an embodiment, the proximal housing 304B can be slid longitudinally either proximally or distally relative to the distal housing 304A to actuate the needle hub 203. It will be appreciated that other configurations of actuating the needle hub 203 such as push buttons, levers, or the like are also contemplated.

With the locking mechanism 340 in the unlocked configuration, the overtube biasing member 366 can urge the overtube 364 distally and transition the overtube 364 from the retracted position to the extended position, either as the needle 204 is withdrawn from the insertion site, or optionally, after the needle is withdrawn from the insertion site. In an embodiment, the biasing member 366 can maintain the overtube 364 in the extended configuration to prevent accidental needle stick injuries. In an embodiment, the needle hub 203 can further include an abutment 368 configured to engage the overtube 364, or portion thereof, and maintain the overtube 364 in the extended configuration to prevent accidental needle stick injuries.

Advantageously, embodiments disclosed herein provide a change in needle outer diameter that is abrupt enough to substantial increase resistance to insertion. This change in insertion resistance indicates the needle tip is correctly placed. In an embodiment, the change in resistance prevents the needle from being inserted past the outer diameter step. This removes any subjective assessment as to when to stop advancing the needle. Accordingly, embodiments can be deployed by users who don't have specialized training or regular practice at placing intraosseous devices. This is especially important since placing intraosseous devices often occur in emergency situations where users may not have specialized training or regular practice, yet need to quickly access a medullary cavity for vascular access.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A needle assembly for an intraosseous access system, comprising:
   a needle hub; and
   a needle coupled to the needle hub, the needle comprising:
      a distal tip;
      an outer surface defining a stepped increase in diameter at a predetermined distance from the distal tip, the stepped increase in diameter configured to penetrate a skin surface and abut against a bone cortex; and
      a lumen comprising:
         a first needle lumen diameter distal of the stepped increase in diameter; and
         a second needle lumen diameter proximal of the stepped increase in diameter, the second needle lumen diameter greater than the first needle lumen diameter.

2. The needle assembly according to claim 1, wherein the predetermined distance is configured to allow the distal tip to extend through the bone cortex and into a medullary cavity of a bone.

3. The needle assembly according to claim 1, wherein the stepped increase in diameter is formed integrally with the needle.

4. The needle assembly according to claim 1, wherein a distal surface of the stepped increase in diameter extends perpendicular to a longitudinal axis of the needle.

5. The needle assembly according to claim 1, wherein a distal surface of the stepped increase in diameter extends at an angle to a longitudinal axis of the needle to define a tapered shape.

6. The needle assembly according to claim 1, wherein the lumen of the needle further comprises a third needle lumen diameter proximal of the second needle lumen diameter, the third needle lumen diameter less than the second needle lumen diameter to define a bulged portion in the needle.

7. The needle assembly according to claim 6, further comprising an obturator disposed within the lumen of the needle, an outer diameter of the obturator being equal to, or less than, the first needle lumen diameter.

8. The needle assembly according to claim 1, further including an overtube engaged with the outer surface of the needle, a distal tip of the overtube defining a portion of the stepped increase in diameter.

9. The needle assembly according to claim 8, wherein a longitudinal length of the overtube is less than a longitudinal length of a shaft of the needle, and wherein the overtube is adhered to the outer surface of the needle to form a collar.

10. The needle assembly according to claim 8, wherein the overtube is slidably or rotatably engaged with the needle.

11. The needle assembly according to claim 8, wherein the overtube includes a material selected from the group consisting of a metal, an alloy, a plastic, a polymer, a composite, and a carbon-based composite.

12. The needle assembly according to claim 8, wherein the overtube includes a first material and a second material different from the first material, wherein the first material is a relatively softer material and can elastically or plastically deform, and wherein the second material is a harder material and can be resistant to any elastic or plastic deformation.

13. The needle assembly according to claim 12, wherein the overtube is formed of concentric tubes comprising:
   a first tube formed of one of the first material or the second material, the first tube disposed adjacent the needle; and
   a second tube formed of one of the first material or the second material, the second tube disposed on an outer surface of the first tube.

14. The needle assembly according to claim 12, wherein the overtube is formed of adjacent tubes including a first tube formed of the first material disposed distally of a second tube formed of the second material.

15. The needle assembly according to claim 12, wherein a first portion of the overtube is formed of the first material and extends annularly about the needle between 1° and 359°, and wherein a second portion of the overtube is formed of the second material and extends annularly about the needle between 1° and 359°.

16. The needle assembly according to claim 8, wherein the distal tip of the overtube is configured to blunt and increase in diameter on contact with a surface of the bone cortex.

17. The needle assembly according to claim 8, wherein a proximal end of the overtube abuts against the needle hub to prevent further longitudinal movement of the distal tip of the needle.

18. The needle assembly according to claim 8, wherein the overtube is slidably engaged with the needle between a retracted position and an extended position, and wherein the distal tip of the overtube extends distally of the distal tip of the needle in the extended position.

19. The needle assembly according to claim 18, further comprising:
   a locking mechanism configured to retain the overtube in the retracted position when in a locked configuration; and
   an actuator configured to transition the locking mechanism between the locked configuration and an unlocked configuration, wherein the actuator is configured for rotating or sliding a proximal housing relative to a distal housing.

20. The needle assembly according to claim 18, further comprising an overtube biasing member configured to bias the overtube toward the extended position.

21. The needle assembly according to claim 20, wherein the overtube biasing member is configured to prevent the overtube from transitioning from the extended position to the retracted position.

22. The needle assembly according to claim 18, further including an abutment configured to engage the overtube in the extended position and prevent the overtube transitioning from the extended position to the retracted position.

23. The needle assembly according to claim 8, wherein one of the needle or the overtube includes graduated markings.

24. The needle assembly according to claim 1, wherein the needle hub includes a proximal housing slidably or rotatably engaged with a distal housing, and wherein the needle hub includes a biasing member configured to bias the distal housing toward a proximal position relative to the proximal housing.

25. The needle assembly according to claim 24, wherein the distal housing includes a distal face configured to engage the skin surface.

* * * * *